United States Patent
Dube et al.

(10) Patent No.: US 11,857,524 B2
(45) Date of Patent: *Jan. 2, 2024

(54) STABLE ORAL SUSPENSIONS OF BACLOFEN

(71) Applicant: ANI Pharmaceuticals, Inc., Baudette, MN (US)

(72) Inventors: Sushant Omprakash Dube, Navi Mumbai (IN); Purushottam Sakhahari Pattewar, Hyderabad (IN); Pankaj Kisan Chatki, Hyderabad (IN); Sumitra Ashokkumar Pillai, Hyderabad (IN)

(73) Assignee: ANI Pharmaceuticals, Inc., Baudette, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/130,597

(22) Filed: Apr. 4, 2023

(65) Prior Publication Data
US 2023/0285341 A1 Sep. 14, 2023

Related U.S. Application Data

(63) Continuation of application No. 18/087,625, filed on Dec. 22, 2022, now Pat. No. 11,696,906, which is a continuation of application No. 17/948,882, filed on Sep. 20, 2022, now Pat. No. 11,564,898, which is a
(Continued)

(30) Foreign Application Priority Data

Apr. 23, 2021 (IN) .............. 202141018869

(51) Int. Cl.
*A61K 31/197* (2006.01)
*A61K 9/00* (2006.01)
*A61K 9/10* (2006.01)

(52) U.S. Cl.
CPC .......... *A61K 31/197* (2013.01); *A61K 9/0053* (2013.01); *A61K 9/10* (2013.01)

(58) Field of Classification Search
CPC .. A61K 31/197; A61K 9/0019; A61K 9/0085; A61K 9/08
See application file for complete search history.

(56) References Cited

U.S. PATENT DOCUMENTS

| 10,610,502 | B1 | 4/2020 | Bryant et al. |
| 2020/0376932 | A1 | 12/2020 | Dubs et al. |
| 2021/0220267 | A1 | 7/2021 | Fallin et al. |

OTHER PUBLICATIONS

"OZOBAX—baclofen solution," Metacel Pharmaceuticals, LLC, 2020, revised Jul. 2021, 12 pages total.

*Primary Examiner* — Savitha M Rao
(74) *Attorney, Agent, or Firm* — Rothwell, Figg, Ernst & Manbeck, P.C.

(57) ABSTRACT

The present invention relates to stable liquid pharmaceutical compositions of baclofen or a pharmaceutically acceptable salt thereof. More specifically, stable oral suspensions of baclofen at concentrations of equal to or more than 2 mg/mL or more are provided. Preferably, the liquid pharmaceutical compositions of baclofen are suitable for oral administration and are stable at wider pH ranges over a variety of storage conditions, including long-term storage for extended periods of time. Methods of treating various disorders using the inventive pharmaceutical compositions are also provided. The invention further relates to various methods for preparing stable suspension of baclofen.

19 Claims, 2 Drawing Sheets

Related U.S. Application Data continuation of application No. 17/591,438, filed on Feb. 2, 2022, now Pat. No. 11,484,518.

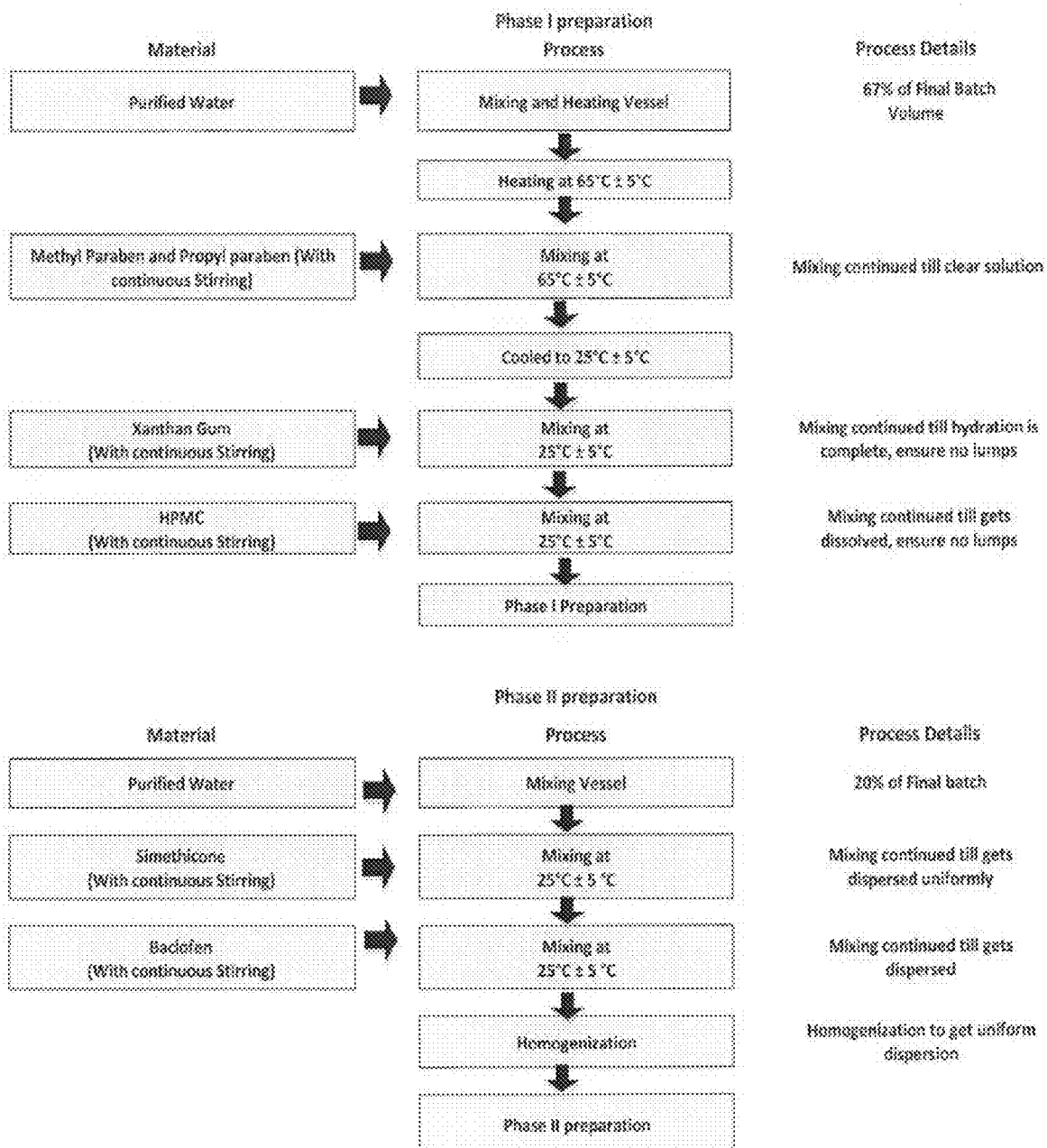
FIG. 1: Brief Manufacturing Process Flow Chart of Phase I and II preparation:

FIG. 2: Brief Manufacturing Process Flow Chart of Phase III preparation and Mixing of Phase I, II and III:
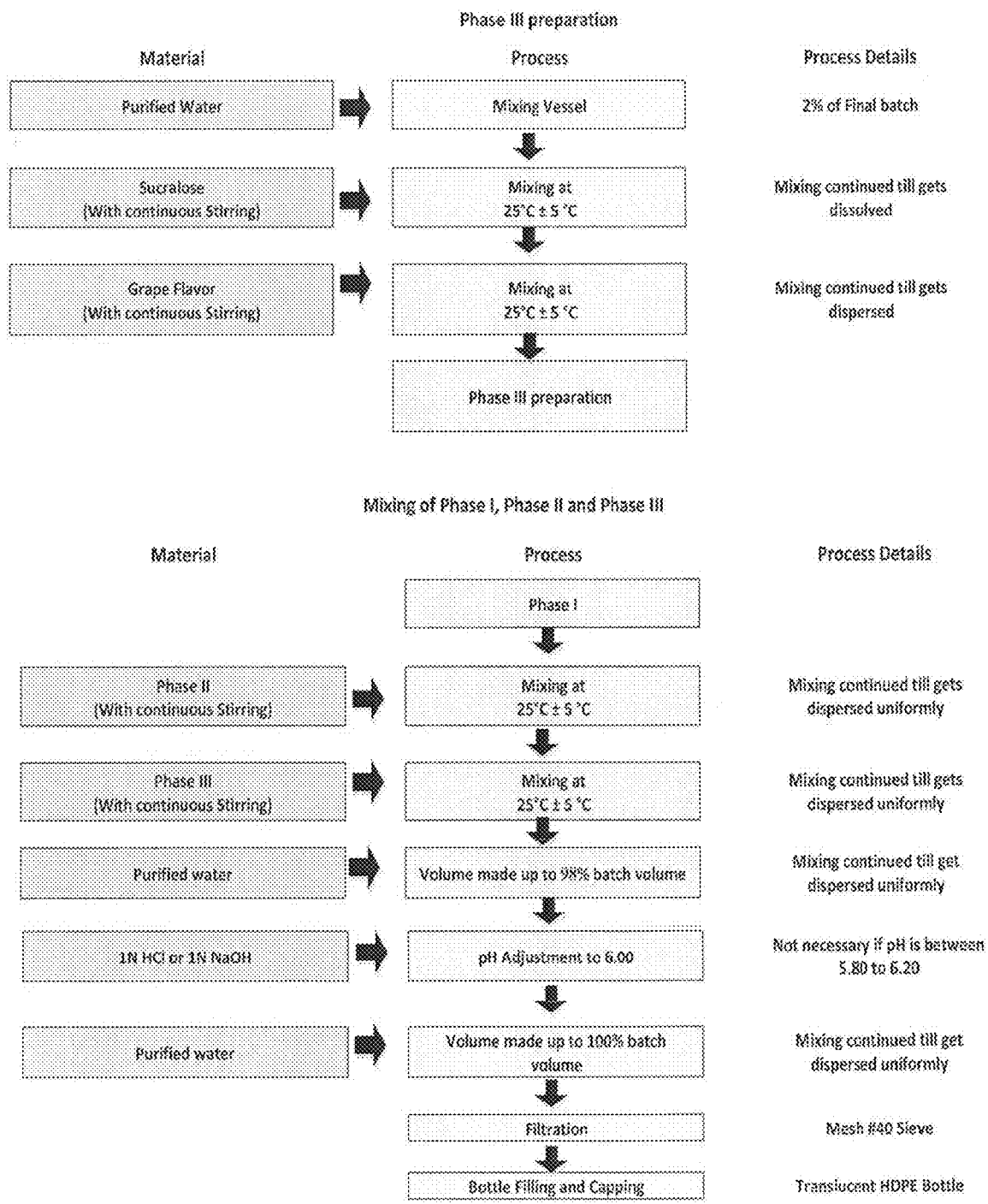

STABLE ORAL SUSPENSIONS OF BACLOFEN

CROSS-REFERENCE TO RELATED APPLICATIONS

This application is a Continuation of U.S. application Ser. No. 18/087,625 filed on Dec. 22, 2022, which is a Continuation of U.S. application Ser. No. 17/948,882 filed on Sep. 20, 2022, now U.S. Pat. No. 11,564,898 issued on Jan. 31, 2023, which is a continuation of U.S. application Ser. No. 17/591,438 filed on Feb. 2, 2022, now U.S. Pat. No. 11,484,518 issued on Nov. 1, 2022, which claims foreign priority to Indian Application No. IN 202141018869, filed on Apr. 23, 2021, which is incorporated herein by reference in its entirety.

FIELD OF THE INVENTION

The present invention relates to stable liquid pharmaceutical compositions of baclofen or a pharmaceutically acceptable salt thereof. More specifically, stable oral suspensions of baclofen at concentrations of equal to or more than about 2 mg/mL are provided. Preferably, the liquid pharmaceutical compositions of baclofen are suitable for oral administration and are stable at a wide range of pH and over a variety of storage conditions, including long-term storage for extended periods of time.

Methods of treating various disorders using the inventive pharmaceutical compositions are also provided. The invention further relates to various methods for preparing a stable suspension of baclofen.

BACKGROUND OF THE INVENTION

Baclofen is a structural analog of the inhibitory neurotransmitter gamma-aminobutyric acid (GABA), and may exert its effects by stimulation of the GABA receptor subtype. Chemically, baclofen is 4-amino-3-(4-chlorophenyl)-butanoic acid, a derivative of Y-aminobutyric acid. It is represented by the following formula:

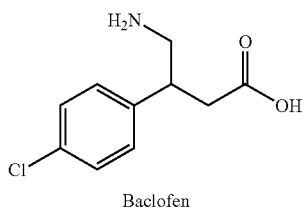 [SMILES: NCC(CC(=O)O)c1ccc(Cl)cc1]

Baclofen

Baclofen is a white to off-white, odourless or practically odourless crystalline powder, with a molecular weight of 213.66 g/mole. It is slightly soluble in water, very slightly soluble in methanol, and insoluble in chloroform.

Baclofen is a skeletal muscle relaxant used to treat spasticity in conditions such as multiple sclerosis or spinal cord injury. Baclofen is currently approved and marketed as intrathecal injection, oral disintegrating tablet, tablet and oral solution dosage forms. KEMSTRO® (baclofen oral disintegrating tablet; 10 mg & 20 mg strengths), LIORESAL® (baclofen tablet; 10 mg & 20 mg strengths) and OZOBAX® (baclofen oral solution; 1 mg/mL strength) were approved in United States for the alleviation of signs and symptoms of spasticity resulting from multiple sclerosis, particularly for the relief of flexor spasms and concomitant pain, clonus, and muscular rigidity. Baclofen intrathecal injection is approved for use in the management of severe spasticity in adult, geriatric, and pediatric patients from age 4 years and above.

The maximum recommended dosage for OZOBAX® (baclofen oral solution; 1 mg/mL) is 80 mg daily (20 mg four times a day). As a result, approximately 80 mL OZOBAX® needs to be administered per day in order to achieve the maximum recommended dosage of baclofen. Spasticity in conditions such as multiple sclerosis or spinal cord injury is a chronic condition, requiring large volumes of baclofen solution to be administered, resulting in poor patient compliance. Therefore, it would be useful to have a higher concentration liquid pharmaceutical composition in order to reduce the overall volume required for oral administration of therapeutic dose. However, baclofen has been difficult to formulate due to its solubility.

In this regard, baclofen dissolves poorly in water, and once dissolved, has a tendency to precipitate out of suspension under normal storage conditions. Baclofen is also extemporaneously compounded as oral suspensions in the hospital pharmacies at concentrations of equal to or more than 5 mg/mL. The extemporaneously compounded oral suspensions of baclofen are not suitable for long-term storage. Moreover, sedimentation of solids is a common problem, which is encountered in oral suspension products, which leads to caking (formation of compact mass), making it difficult to dispense the suspension.

Further, the content of active ingredient depends to a large extent upon the re-dispersibility of the oral suspension product. Lack of stable, uniformly dispersed liquid formulations leads to dose uniformity issues that can result in patients receiving a dose of baclofen that is more or less than the recommended dose. An overdose of baclofen in patients may cause coma or with progressive drowsiness, lightheadedness, dizziness, somnolence, accommodation disorders, respiratory depression, seizures, or hypotonia progressing to loss of consciousness.

Administration of solid oral dosage forms to pediatric and geriatric population still remains a challenge, particularly due to a frequent lack of age-appropriate formulations, which raises a concern about dose accuracy. Moreover, several factors specific to the pediatric and geriatric population, such as the ability to swallow, palatability issues, etc., may hamper the administration of oral medication. Indeed, most commercially available medicines are designed for adults and do not provide ease of use for pediatric and geriatric population. Beyond the efforts of health authorities to promote the development of pediatric and geriatric medicines, many medicinal products are authorized only for adults and are not currently available in formulations suitable for administration to pediatric and geriatric population. Consequently, caregivers or parents frequently modify medicines, which are used off-label for administration in children, leading to dose error risk or inaccurate dosing, as well as stability and/or bioavailability issues pertaining to the drug.

In general, there is a need for developing oral liquid formulations of baclofen that allow for dosing flexibility which can cater to the needs of geriatric and pediatric population. There is an increased recognition that for medicines requiring precise dosage and titration, as with baclofen, development of oral liquid formulations allow for tailored dosages across the dosing range. In the absence of a ready-made product, there are several approaches that are utilized in an attempt to "create" an appropriate dosage form for pediatric and geriatric population. One frequent approach is to prepare an oral liquid from tablets, capsules or powdered drug dispersed or dissolved in a suitable base. The practice of crushing tablets or opening capsules and adding the powder to a drink (e.g., water, juice or soda) or sprinkling on solid food (e.g., apple sauce or pudding) is an alternative, but there are few circumstances where this method is appropriate. It is difficult to ensure that a complete dose has been taken, the effects on the drug from the food or drink the tablet is dispersed into are unknown, and the practice of nurses, caregivers or other healthcare professionals handling powdered drug may pose significant health concerns. With baclofen doses ranging from 1 mg to 400 mg per day, utilizing the currently available 5, 10, and 20 mg tablets presents significant challenges in drug delivery to the pediatric or geriatric population. For example, to deliver a 15 mg dose or any dose greater than 20 mg, multiple tablets and significant manipulation of the tablets is required to deliver these doses.

Drugs are formulated as suspensions for many different reasons, but a common reason is poor drug solubility. Suspensions may also be used to mask the poor taste resulting from the dissolved drug in solution. A suspension, however, unlike syrup in which the drug is fully dissolved, may require adequate shaking of the container to resuspend the drug uniformly before dosing. Difficult redispersion of the drug from a sediment, or in the worst case, from caking, will result in under- and overdosing. This problem of variable dosing is also encountered when the patient or the caregiver forgets to shake the container before dosing. It is therefore desirable to produce a suspension that is able to maintain its homogeneity on prolonged storage without requiring shaking prior to use.

Generally, if particles with a wide range of sizes are dispersed in a medium there will be a differential rate of dissolution of the particles in the medium. The differential dissolution results in the smaller particles being thermodynamically unstable relative to the larger particles and gives rise to a flux of material from the smaller particles to the larger particles. The effect of this is that the smaller particles dissolve in the medium, whilst the dissolved material is deposited onto the larger particles thereby giving an increase in particle size. One such mechanism for particle growth is known as Ostwald ripening.

The growth of particles in a dispersion can result in instability of the dispersion during storage resulting in the sedimentation of particles from the dispersion. It is particularly important that the particle size in a dispersion of a pharmacologically active compound remains constant because a change in particle size is likely to affect the bioavailability, toxicity and hence the efficacy of the compound.

Theoretically, particle growth resulting from Ostwald ripening would be eliminated if all the particles in the dispersion were of the same size. However, in practice, it is impossible to achieve a completely uniform particle size and even small differences in particle sizes can give rise to particle growth.

Reducing the particle size is another way of slowing sedimentation. However, small particles tend to cake more severely because of the increased surface energy from the larger surface area, making redispersion much more difficult and sometimes impossible.

Small particle size is desirable for reasons other than slowing the rate of sedimentation. For drugs that are not very soluble, smaller particles generally dissolve faster due to the increase in the total surface area, which can in turn enhance bioavailability. Also, smaller drug particles are less likely to cause grittiness, which improves the palatability of the finished product. There is therefore a need for a suspension containing fine particles, which will not cake on storage, but in addition is able to maintain its homogeneity on prolonged storage without requiring shaking.

The most popular approach to slowing the sedimentation rate is by increasing the viscosity through the addition of a suspending agent. However, excessive viscosity is undesirable as it interferes with pouring and re-dispersibility of settled particles.

Formation of foam during the preparation of liquid formulation is also a common problem as it interferes with development of stable and effective liquid formulation. The severity of foam formation depends on nature of active ingredients as well as other excipients used in the preparation.

Accordingly, it would be useful to develop stable aqueous suspensions of baclofen suitable for oral administration at concentrations of equal to or more than 2 mg/mL that have a useful shelf life and are easily re-suspended if caking/settling occurs. Additionally, the suspensions should be easy to pour, pleasant in appearance and taste, stable for an extended period of time, and free of microbial contamination.

Further, U.S. Patent Publication No. 20210220267 disclose liquid compounded formulations of baclofen and diluents that can be used by a pharmacist to reconstitute baclofen. The disclosed formulations are not ready-to-use preparations and have to be extemporaneously prepared by pharmacists. Hence, there still is a need for a stable liquid ready-to-use dosage form of baclofen.

Despite many attempts to design a liquid dosage form of baclofen, up to now, there is no commercial ready-to-use liquid formulation of baclofen with concentration 2 mg/mL or more meeting health regulatory authorities requirements. This is probably due to the drug sensitivity in the liquid medium and lack of data on prolonged stability of the active compound in such medium over sufficient time to allow the design and the marketing of a viable commercial product.

It is therefore an object of the present invention to provide a pharmaceutical formulation that is suitable for the preparation of a ready-to-use liquid formulation. The ready-to-use formulation shall prevent the potential side effects that can be elicited by extemporaneous formulations which are not well characterized. The liquid formulation shall be suitable for the formulation of a wide variety of drugs and, in particular, for the formulation of drugs which have hydrophobic and/or lipophilic properties and/or exhibits stability problems in aqueous environment. Said formulation shall allow an accurate and precise dosing of the drug contained therein and shall be particularly suitable in the medical treatment of patient groups with swallowing problems such as pediatric or elderly patients. The drug shall be stable within said preparation for a long shelf-life.

There appears to be a clinical need for providing stable aqueous suspensions of baclofen suitable for oral administration at concentrations of equal to or more than 2 mg/mL, having acceptable pharmaceutical properties, and most preferably, suspensions that are stable in a variety of storage conditions for extended periods of time.

From the above discussions, it is evident that there is a need for development of a ready-to-use or ready-to-administer oral liquid composition of baclofen which would not only minimize the risk of potential medication preparation errors, but also reduces the preparation-associated costs. In addition, bulk preparation would save nursing time and avoid delays in timely administration of baclofen.

What is needed is an aqueous suspension of baclofen suitable for oral administration at concentrations of equal to or more than 2 mg/mL, which is stable at wider pH ranges, over a variety of storage conditions, including long-term storage for extended periods of time.

SUMMARY OF THE INVENTION

In an aspect, liquid pharmaceutical composition suitable for oral administration comprises baclofen, a pharmaceutically acceptable excipient, and at least one pharmaceutically acceptable liquid vehicle, wherein baclofen is present at a concentration of equal to or more than 2 mg/mL, and wherein the liquid pharmaceutical composition is stable.

In particular, a stable liquid suspension is provided, comprising: baclofen; at least one stabilizer, and at least one pharmaceutically acceptable liquid vehicle; wherein a concentration of the baclofen is 2 mg/mL or more, and wherein the suspension is suitable for oral administration to a subject in need thereof. Preferably, the suspension has a pH ranging from about 4.0 to about 8.0. Preferably, the suspension is in the form of a ready-to-use or ready-to-administer stable liquid suspension that is suitable for oral administration to a subject in need thereof. Preferably, the level of 4-(4-chlorophenyl)-2-pyrrolidinone in the suspension is less than about 2% (w/w) as measured by HPLC when stored for 3 months at 25° C./60% RH. Preferably, the suspension further comprising at least one suspending agent and/or an anti-foaming agent. For example, in certain aspects, the anti-foaming agent is a simethicone emulsion, and may be present in an amount that ranges from 0.01% w/w to 1% w/w, preferably in an amount of 0.05% w/w.

In an embodiment, the liquid pharmaceutical composition is a suspension.

In another embodiment, the liquid pharmaceutical composition is an aqueous or non-aqueous suspension.

In another aspect, stable aqueous suspensions suitable for oral administration comprises (a) baclofen; (b) pharmaceutically acceptable liquid vehicle; and (c) one or more pharmaceutically acceptable excipients, selected from the group consisting of stabilizers, pH adjusting agents, buffering agents, solubilizers, suspending agents, anti-oxidants, anti-foaming agents, chelating agents, surfactants, preservatives, flavoring agents, sweetening agents, coloring agents, and mixtures thereof.

In an aspect, stable aqueous suspensions suitable for oral administration comprises baclofen, pharmaceutically acceptable liquid vehicle, suspending agent and one or more additional pharmaceutical acceptable excipients.

In another aspect, stable aqueous suspensions suitable for oral administration comprises baclofen, pharmaceutically acceptable liquid vehicle, stabilizer and one or more additional pharmaceutical acceptable excipients.

In yet another aspect, stable aqueous suspensions suitable for oral administration comprises baclofen, pharmaceutically acceptable liquid vehicle, at least one stabilizer, at least one suspending agent and one or more additional pharmaceutical acceptable excipients.

The inventive compositions are advantageously ready-to-administer (RTA). An aspect of the invention relates to stable ready-to-administer (RTA) baclofen compositions suitable for oral administration.

Another aspect relates to methods of treatment using the inventive suspension compositions. Specifically provided is a method for managing or treating or alleviating the signs and symptoms of spasticity resulting from multiple sclerosis or spinal cord damage or spinal cord disease in a patient by orally administering effective amount inventive suspension compositions, to an adult, pediatric or geriatric patient.

Each aspect above may further have one or more of the following additional elements in any combination:

Element 1: wherein baclofen is present at a concentration of 2 mg/mL or more. Preferably, the baclofen is present at a concentration of about 2 mg/mL to about 20 mg/mL, preferably about 5 mg/mL or more.

Element 2: wherein the pharmaceutical composition is aqueous suspension. In certain embodiments, the pharmaceutical composition is a non-aqueous suspension.

Element 3: wherein the pharmaceutically acceptable excipient is selected from the group consisting of a suspending agent, a stabilizer, a sweetening agent, a flavoring agent, a preservative, an anti-foaming agent, an antioxidant, a pH adjusting agent, a buffering agent, a coloring agent, a surfactant and mixtures thereof.

Element 4: wherein the suspending agent is selected from the group consisting of microcrystalline cellulose, carboxymethylcellulose sodium, ethyl cellulose, hydroxyethyl cellulose, methylcellulose, methyl ethyl cellulose, sodium carboxymethylcellulose, colloidal silicon dioxide, cetostearyl alcohol, cetyl alcohol, stearyl alcohol, stearyl alcohol carbomer, locust bean gum, maltodextrin, acacia, tragacanth, polyvinyl alcohol and mixtures thereof.

Element 5: wherein the stabilizer is selected from the group consisting of hydroxypropyl methylcellulose (HPMC), hydroxypropylcellulose (HPC), povidone (PVP K-30), poloxamer and combinations thereof.

Element 6: wherein the aqueous suspension has a pH in the range of about 5 to about 8, preferably between about 5 to about 7. In certain embodiments, the liquid suspension has a pH in the range of about 4 to about 8, preferably between about 5 to about 7, more preferably between about 6 to about 7.

Element 7: wherein the aqueous suspension is stable for at least 6 months at about 2-8° C., or 25° C./60% relative humidity (RH) condition or is stable for at least 6 months at 40° C./75% relative humidity (RH) conditions. In certain embodiments, the aqueous suspension is stable for at least 12 months at about 2-8° C., or 25° C./60% relative humidity (RH) condition or is stable for at least 12 months at 40° C./75% relative humidity (RH) conditions.

Element 8: wherein the level of impurities in the aqueous suspension is less than about 5% (w/w), less than about 4% (w/w), less than about 3% (w/w), less than about 2% (w/w), preferably less than about 1.5% (w/w), more preferably less than about 1% (w/w) as measured by HPLC. Preferably, the level of 4-(4-chlorophenyl)-2-pyrrolidinone in the suspension is less than about 2% (w/w) as measured by HPLC when stored for 3 months at 25° C./60% RH. In certain embodiments, a level of (4-(4-chlorophenyl)-2-pyrrolidinone is less than about 2% (w/w), preferably less than about 1.5% (w/w), more preferably less than about 1% (w/w) as measured by HPLC.

Element 9: wherein baclofen is present in micronized form having a particle size of less than 100 micrometers.

By way of non-limiting example, exemplary combinations applicable to the embodiments described in this application may include any combination with one or more of Elements 1-9, described above.

BRIEF DESCRIPTION OF THE DRAWINGS

FIG. 1 illustrates the Manufacturing Process Flow Chart of Phase I and II preparation.

FIG. 2 illustrates the Manufacturing Process Flow Chart of Phase III preparation and Mixing of Phase I, II and III.

DETAILED DESCRIPTION OF THE INVENTION

Unless defined otherwise, all the technical and scientific terms used herein have the same meanings as commonly known by a person skilled in the art. In the case that there is a plurality of definitions for the terms herein, the definitions provided herein will prevail.

As used herein the term "baclofen" refers to baclofen free base or a pharmaceutically acceptable salt, solvate or hydrate thereof. It also includes a geometric isomer or a stereoisomer thereof. In certain embodiments, baclofen free base may be used. Any crystalline form of baclofen as well as the amorphous form may be used for the preparation of pharmaceutical compositions of the present invention.

The terms "about" and "approximate", when used along with a numerical variable, generally means the value of the variable and all the values of the variable within an experimental error (e.g., 95% confidence interval for the mean) or within a specified value ±10% or within a broader range. However, when the term "about" is used in connection with pH, it should be considered as ±2 unit of the pH value. The use of the term "or" in the claims is used to mean "and/or" unless explicitly indicated to refer to alternatives only or the alternatives are mutually exclusive, although the disclosure supports a definition that refers to only alternatives and to "and/or". The terms "comprise", "have", and "include" are open-ended linking verbs. Any forms or tenses of one or more of these verbs "comprises," "comprising," "has," "having," "includes," and "including" are also open-ended. For example, any method that "comprises," "has" or "includes" one or more steps is not limited to possessing only those one or more steps and also covers other unlisted steps.

The terms "composition", "pharmaceutical composition", "pharmaceutical product", "dosage form", "pharmaceutical dosage form", "formulation", "pharmaceutical formulation", etc., are used interchangeably and refer to unit dosage form administered to a patient in need of treatment. For example, the term "pharmaceutical composition" as used herein includes an aqueous suspension.

The term "pharmaceutically acceptable" substances mean those, which, according to a common medical judgment, are suitable to be in contact with a tissue of a patient without any inappropriate toxicity, irritation, allergic response, etc., have a reasonable balance between advantages and disadvantages, and can be applied to its target use effectively.

"Optional" or "optionally" may be taken to mean that the subsequently described structure, event or circumstance may or may not occur, and that the description includes instances where the events occurs and instances where it does not.

In embodiments, the pharmaceutically acceptable liquid vehicle can be but not limited to, for example, water, purified water, isopropyl alcohol, methanol, acetone, ethanol, 1-propanol, butanediol or combinations thereof.

The term "effective amount" refers to that amount which is sufficient to effect treatment, as defined herein, when administered to a subject in need of such treatment. The effective amount will vary depending on the subject and disease state being treated, the severity of the affliction and the manner of administration, and may be determined routinely by one of ordinary skill in the art.

As used herein, "to treat" a condition or "treatment" of the condition is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

Within the context of this invention, the term "suspension" refers to a mixture of one or more substances dispersed molecularly in a dissolving liquid medium or vehicle. The suspension is preferably homogeneous, in the sense that each API is essentially uniformly distributed and concentrated in the suspension. As already mentioned, a liquid suspension differs from a solution which comprises solid particles dispersed throughout a liquid phase in which they are not soluble. As used herein, a "particle" may be a crystal, a granule, an agglomerate, or any undissolved solid material.

As used herein "aqueous suspension" means a suspension that is at least 60% water by weight, 70% water by weight, preferably at least 80% water by weight, more preferably at least 95% water by weight and most preferably at least 98% water by weight.

The terms "stable" and "stability" mean that the evolution of the product with time and/or under specific environmental conditions (i.e., temperature, humidity, etc.) has no significant effects on its concentration, quality, safety and/or efficacy for a given time period. Stability can be measured through the formation of degradation products (impurities), variation of pH, appearance (sedimentation, agglomeration or cake formation), microbial growth, and/or color. The term "stable" indicates both chemical and physical stability.

The term "degradation product," as used herein, refers to an unwanted chemical or impurity (including, but not limited to known or unknown related substances) that can develop during the manufacturing, transportation, and storage of drug products and can affect the efficacy of pharmaceutical products. It can form in response to changes in oxygen, light, temperature, pH, and humidity, or due to inherent characteristics of active ingredient, such as their reaction with excipients or on contact with the packaging.

The term "ready-to-use" as used herein, refers to a formulation that does not require reconstitution or dilution or mixing with a prescribed quantity of liquid diluent, e.g., purified water or any other suitable liquid diluents (For example, but not limited to simple syrup, Ora-plus syrup, Aromatic Elixir, water for injection, 0.9% saline (normal saline), 0.45% saline (half normal saline), 2.5% dextrose/ 0.45% saline, 5% dextrose solution, Ringer's solution and Ringer's lactate solution), before use by the oral route. The formulation of the present disclosure ready to be administered and can be directly administered without the need for any intervening steps of reconstitution and/or dilution or mixing.

The term "ready-to-administer" as used herein, refers to a formulation that does not require any steps or handling or manipulation before administration and can be directly administered orally to the patient.

The terms "ready-to-use" and "ready-to-administer" can be used interchangeably.

The present application relates to stable ready-to-administer (RTA) or ready-to-use (RTU) baclofen compositions suitable for oral administration comprising baclofen and one or more pharmaceutically acceptable excipient.

The present application relates to a stable liquid suspension of baclofen, particularly wherein baclofen is present at a concentration of 2 mg/mL or more. In one embodiment, a pharmaceutical composition of the present application comprises baclofen, wherein baclofen concentration is about 2 mg/mL to about 20 mg/mL, and preferably about 3 mg/mL or more, about 4 mg/mL or more, about 5 mg/mL or more, about 6 mg/mL or more, about 7 mg/mL or more, about 8 mg/mL or more, about 9 mg/mL or more, or about 10 mg/mL or more. In particular, the present invention provides stable aqueous baclofen suspensions for oral administration, wherein baclofen is present at a concentration equal to, or about: 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.5, 7.0, 7.5, 8.0, 8.5, 9.0, 9.5, 10.0, 10.5, 11.0, 11.5, 12.0, 13, 14, 15, 16, 17, 18, 19 and 20 mg/mL, and preferably 5 mg/mL.

Any appropriate form of baclofen can be used to prepare oral suspensions of the present invention. For example, any crystalline or amorphous form of baclofen may be used in the pharmaceutical compositions of the present application. In other embodiments, the baclofen can be provided as an aqueous or non-aqueous suspension of baclofen, including buffered suspensions.

In an embodiment of the present invention, a stable liquid suspension suitable for oral administration comprising baclofen, wherein baclofen is in micronized form having a particle size of less than 100 micrometers. The particles of baclofen can be obtained for example by micronization or by milling. Preferably the particles are obtained by micronization. In an embodiment, the D90 particle size of baclofen can be in the range of 10 to 200 microns. Preferably, the D90 particle size of baclofen can be between 30 and 100 microns.

In certain non-limiting embodiments of the invention, a stable liquid suspension suitable for oral administration comprising baclofen and at least one stabilizer. In certain embodiments, suitable stabilizers include but are not limited to hydroxy propyl methylcellulose (HPMC), hydroxypropylcellulose (HPC), polyvinylpyrrolidone (PVP K-30), poloxamer and mixtures thereof. The concentration of stabilizer ranges from about 1 mg/mL to about 30 mg/mL, preferably from about 5 mg/mL to about 20 mg/mL, more preferably 5 mg/mL to 10 mg/mL.

In yet another embodiment of the present invention, a stable liquid suspension suitable for oral administration comprising baclofen and suspending agent. In certain embodiments, the suspending agent may be selected from the group consisting of microcrystalline cellulose, carboxymethylcellulose sodium, ethyl cellulose, hydroxyethyl cellulose, methylcellulose, methyl ethyl cellulose, sodium carboxymethylcellulose, colloidal silicon dioxide, cetostearyl alcohol, cetyl alcohol, stearyl alcohol, stearyl alcohol carbomer, locust bean gum, maltodextrin, acacia, tragacanth, polyvinyl alcohol and mixtures thereof. The concentration of suspending agent ranges from about 1 mg/mL to about 30 mg/mL, preferably from about 1 mg/mL to about 10 mg/mL, more preferably about 5 mg/mL to 10 mg/mL.

In an embodiment of the present invention, a stable liquid suspension suitable for oral administration comprising baclofen can be formulated at any suitable pH. Baclofen undergoes hydrolysis resulting in increased impurity formation at very high or very low pH values. Hence, it is very important to maintain pH of baclofen suspension in the range of 4 to 8, preferably from about 5 to about 7 for achieving desired stability.

The inventive liquid pharmaceutical composition will be provided in a dosage form that is suitable for oral administration, i.e., aqueous suspension. The suspensions may be formulated according to conventional pharmaceutical practice.

In an embodiment, one or more pharmaceutically acceptable excipients combined with baclofen comprises stabilizers, suspending agents, sweetening agents, flavoring agents, preservatives, anti-oxidants, pH adjusting agents, buffering agents, coloring agents, anti-foaming agents, surfactants and combinations thereof.

In one embodiment of the present invention, a stable aqueous suspension suitable for oral administration comprising baclofen and a suspending agent, where in the suspension further comprises additional pharmaceutically acceptable excipients. In another embodiment, the present application provides an aqueous suspension comprising baclofen and a stabilizer, where in the suspension further comprises additional pharmaceutically acceptable excipients.

In another embodiment of the present invention, a stable aqueous suspension suitable for oral administration comprising baclofen, at least one stabilizer, wherein the weight ratio of baclofen to stabilizer ranges from about 1:0.25 to about 1:5 preferably from about 1:1, about 1:3, more preferably about 1:2.

In yet another embodiment, stable aqueous suspensions of the present application comprise baclofen, at least one suspending agent, the composition further comprises additional pharmaceutically acceptable excipients, wherein the weight ratio of baclofen to suspending agent ranges from about 1:0.25 to about 1:5, preferably 1:0.5 to about 1:2, more preferably from about 1:0.5 to about 1:0.9.

In an embodiment, the invention relates to aqueous suspensions of baclofen intended for oral administration comprising baclofen at a concentration of equal to or more than 2 mg/mL or more and at least one pharmaceutically acceptable excipient, wherein the suspension has a pH in between about 5 to about 7 and wherein the suspension is stable for at least 6 months at 40° C./75% RH.

In an embodiment, the invention relates to aqueous suspensions of baclofen intended for oral administration comprising baclofen at a concentration of about 5 mg/mL and at least one pharmaceutically acceptable excipient, wherein the suspension has a pH in between about 5 to about 7, and wherein the composition is stable for at least 6 months at 2° C.-8° C. or for at least 12 months at 25° C./60% RH.

The inventive stable suspensions comprise baclofen, xanthan gum, hydroxypropylmethylcellulose, simethicone emulsion, one or more preservatives, one or more sweeteners and/or flavorings and water. While not excluding the possibility that other ingredients contribute to the stability of the formulation, in one embodiment, hydroxypropylmethylcellulose is included to stabilize the active ingredient. Similarly, in another embodiment, the use of simethicone contributes to stability by minimizing the formation of foam on mixing or agitation during formulation, or incidentally during transport, use, and storage. While not wishing to be bound by theory, the formation of foam could be associated with condition such as denaturing the API or conditions that would diminish the patient's ability to measure an exact dose.

In an embodiment, an anti-foaming agent is included in the composition to minimize the amount of foam produced during manufacture of the composition. The suitable anti-foaming agents include but are not limited a silicon-based agent, such as for example simethicone emulsion. Simethicone emulsion is a water-dilutable, non-ionic emulsion containing about 30% simethicone, about 1-5% silica gel, about 1-5% polyethylene glycol stearate, and water. The simethicone emulsion may be present in an amount that ranges from 0.01% w/w to 1% w/w, and all amounts in between, including, for example, 0.02% w/w, 0.03% w/w, 0.04% w/w, 0.05% w/w. In a particular embodiment, simethicone emulsion is present in an amount of 0.05% w/w.

In embodiments, the suitable solubilizers include but are not limited to propylene glycol, polyethylene glycol, glycerol, Tween 20, Tween 80, sodium lauryl sulfate (SLS) or combinations thereof.

In an embodiment, suitable pH adjusting agents include but are not limited to acetic acid; ammonia suspension, strong; acetic acid, glacial; ammonium carbonate; citric acid, anhydrous; diethanolamine; citric acid monohydrate; potassium hydroxide; fumaric acid; sodium bicarbonate; hydrochloric acid; sodium borate; hydrochloric acid, diluted; sodium carbonate; malic acid; trolamine; phosphoric acid; sodium hydroxide; nitric acid; phosphoric acid, diluted; propionic acid; sulfuric acid; tartaric acid; or mixtures thereof.

In an embodiment, suitable buffering agents include acetic acid; adipic acid; ammonium carbonate; ammonium phosphate; boric acid; citric acid anhydrous; citric acid monohydrate; lactic acid; phosphoric acid; potassium citrate; potassium metaphosphate; potassium phosphate, dibasic; potassium phosphate, monobasic; sodium acetate; sodium citrate; sodium lactate suspension; sodium phosphate, dibasic; sodium phosphate, monobasic; succinic acid or mixtures thereof.

In an embodiment, suitable sweetening or flavoring agents include xylitol, aspartame, sucralose, and the like and/or cherry flavor, artificial banana flavor, caramel, chocolate mint flavor, grape flavor, wild cherry flavor, raspberry flavor, strawberry flavor, mixed berry flavor, citrus flavor, orange flavor, pineapple flavor, citrus lime flavor, citrus cream flavor, cherry vanilla flavor, creme de menthe flavor and mixtures thereof.

As used herein, "anti-oxidant" refers to an agent which inhibits oxidation and thus is used to prevent the deterioration of preparations by the oxidative process. Such compounds include by way of example and without limitation, sodium bisulfate, ascorbic acid, ascorbyl palmitate, citric acid, tartaric acid, glycine, L-cysteine hydrochloride, L-methionine, butylated hydroxy anisole (BHA), butylated hydroxytoluene (BHT), hydro phosphorous acid, monothioglycerol, propyl gallate, sodium ascorbate, sodium citrate anhydrous, sodium citrate dihydrate, sodium sulfide, sodium sulfite, sodium bisulfite, sodium formaldehyde sulfoxylate, thioglycolic acid, sodium metabisulfite and mixtures thereof.

Preservatives cause biocidal or biostatic activity, such that a low bioburden is maintained in the formulation of the invention from preparation through storage, and during routine use by patients and clinicians. In an embodiment, suitable preservatives include anti-microbials and agents that enhance sterility. Exemplary preservatives include ascorbic acid, ascorbyl palmitate, benzyl alcohol, butylated hydroxy anisole (BHA), butylated hydroxytoluene (BHT), citric acid, erythorbic acid, fumaric acid, malic acid, propyl gallate, sodium ascorbate, sodium benzoate, sodium bisulfate, sodium metabisulfite, sodium sulfite, parabens (methyl-, ethyl-, propyl-, butyl-), benzoic acid, potassium sorbate, and vanillin.

A "chelating agent" according to the disclosure is preferably an agent which forms via two or more of its functional groups stable complexes with metal cations, e.g., preferably a poly-acetic acid or a pharmaceutically acceptable salt thereof like disodium EDTA and DTPA. Chelating agents are capable of forming more than one bond. Ethylene diamine, for example, is bidentate (two links), tripyridyl is tridentate (three) and disodium ethylene diamine tetra acetic acid (disodium EDTA) is hexadentate (six) which makes it particularly effective as a pharmaceutical chelating agent. One of the consequences of chelation typically is the formation of a cyclic structure, which may have high thermodynamic and thermal stability.

Preferably the chelating agent is a bivalent cation chelator and more preferably, the chelator is selected from the group consisting of disodium ethylenediaminetetraacetic acid (disodium EDTA), diethylenetriaminepentaacetic acid (DTPA), ethylene glycol-bis (β-amin oethyl ether)-tetra acetic acid (EGTA), N-(hydroxyethyl) ethylenediaminetriacetic acid (HEDTA), nitrilotriacetic acid (NTA), triethanolamine, 8-hydroxyquinoline, phosphoric acid, gluconic acid, saccharic acid, thiodipropionic acid, acetonic dicarboxylic acid, lecithin, di(hydroxyethyl)glycine, phenylalanine, tryptophan, glycerine, sorbitol and pharmaceutically acceptable salts thereof. More preferably, the chelating agent is selected from the group consisting of disodium EDTA, DTPA, phosphoric acid, gluconic acid or a pharmaceutically acceptable salt thereof. The amount of chelating agent may range from about 0.1 mg/mL to about 1 mg/mL of the composition.

A key problem in devising oral liquid formulations that are practical, safe, and effective to make and use, is the balance required between palatability and the handling requirements of the dose form on the one hand, and the stability of the formulation and the homogeneity of the doses on the other. Where, as in the present invention, it is desired to produce a liquid medication for oral delivery in a series of doses spread over time, it is critical to provide a formulation in which the potency of the active ingredient remains acceptably constant over the time that the formulation is to be used, so that from the first dose to last dose, the same dose of active ingredient is delivered per unit volume of the formulation dosed to the patient. In addition, as in the case of the present invention where the API is presented as a suspension in a liquid formulation, it is necessary that the formulation is capable of providing homogenous doses. That is, that the active ingredient does not clump, settle to the bottom, float to the top, or stick to the sides of the container or any dosing or manufacturing device in a manner that would cause the dose of active ingredient contained in unit volume doses obtained from the preparation to vary unacceptably. It is generally desirable for the formulation to be sufficiently pleasant for the patient to consume and assure compliance with the regimen prescribed by the clinician, where the dose is delivered orally. It is generally desirable for the viscosity of the liquid formulation to be low enough to facilitate handling of the formulation in the manufacture, storage, and dosing in a manner such that there are not unacceptable losses of drug, i.e., material adhering to the containers or equipment used for manufacture and storage or by adherence or clumping within the drug delivery device such as a nasogastric feeding tube. If too much drug adheres to and clumps on equipment and containers used to make, store, and deliver doses, then the delivery of active ingredient to the patient becomes unreliable, which undermines the consistency, efficacy, and safety of therapy.

An advantage of the invention is the flexibility of dose that can be prescribed by the physician and provides ease of use to healthcare providers and patient. The ability to use the liquid formulations of the invention also offers advantages to physicians, as it provides the ability to prescribe with more flexibility for a range of challenging and otherwise vulnerable patients. The palatability of the disclosed formulations improves patient compliance and minimizes patient distress. The liquid nature of the formulations disclosed allows the dosing of baclofen to children and elderly patients who are unable to reliably swallow capsules. Furthermore, the liquid nature of the formulations disclosed allows the dosing of baclofen to critical care patients who are otherwise unable to swallow capsules due to intubation or other injuries, pathologies, or interventions that inhibit the ability to receive or take medication in solid format.

In an embodiment, a process for preparing pharmaceutical compositions of the present invention comprises: a) pharmaceutically acceptable vehicle was heated to 60° C.±2° C. in a suitable container; b) preservatives were added to the purified water at 60° C.±2° C. and stirred continuously to obtain a preservative solution, where the preservative solution was kept for cooling under continuous mixing until the temperature was reduced to 25° C.±2° C.; c) suspending agent was added to preservative solution and mixed continuously to obtain a solution; d) stabilizer was added to solution obtained in step c) and mixed continuously to obtain a Phase-I solution; e) anti-foaming agent was added to purified water in a separate container and stirred continuously; f) add required quantity of active ingredient to step e) dispersion to obtain a Phase II dispersion; g) sweetening agent was added to purified water in a separate container and stirred continuously to obtain clear solution; h) flavoring agent was added to solution obtained step g) and stirred continuously to obtain a Phase-III solution. i) Phase-II dispersion was added to Phase-I solution and stirred continuously to obtain a pre-final suspension; j) Phase-III solution was added to pre-final suspension and stirred continuously to obtain a final suspension whose volume was made up by adding required quantity of pharmaceutically acceptable vehicle and pH was adjusted to desired pH range by using pH adjusting agent.

In an embodiment, a process for preparing pharmaceutical compositions of the present invention comprises: a) purified water was heated to 60° C.±2° C. in a suitable container; b) methyl paraben and propyl paraben were added to the purified water at 60° C.±2° C. and stirred continuously to obtain a preservative solution, where the preservative solution was kept for cooling under continuous mixing until the temperature was reduced to 25° C.±2° C.; c) xanthan gum was added to preservative solution and mixed continuously to obtain a solution; d) HPMC was added to solution obtained in step c) and mixed continuously to obtain a Phase-I solution; e) simethicone emulsion was added to purified water in a separate container and stirred continuously; f) add required quantity of baclofen to step e) dispersion to obtain a Phase II dispersion; g) sucralose was added to purified water in a separate container and stirred continuously to obtain clear solution; h) Grape flavor was added to solution obtained step g) and stirred continuously to obtain a Phase-III solution. i) Phase-II dispersion was added to a Phase-I solution and stirred continuously to obtain pre-final baclofen suspension; j) Phase-III solution was added to pre-final baclofen suspension and stirred continuously to obtain final baclofen suspension whose volume was made up by adding required quantity of purified water and pH was adjusted to desired pH range by using NaOH or 1N HCl.

The pharmaceutical compositions of present application may be filled into any suitable pharmaceutically acceptable containers. For example, the pharmaceutically acceptable container may be selected from group consisting of bottles and syringes.

The bottle can be made of any material convenient with the storage and the use requirements comprising polymers, metal and glass and so on. It is of importance that the bottle material does not interfere with the components of the liquid formulation as disclosed herein. In an embodiment it is made of glass. In order to protect the active ingredient from light-induced degradation, a preferred embodiment comprises amber glass bottle.

The bottle capacity can be adapted to the volume to be administrated for the period during which the liquid formulation as disclosed herein is stable. For instance, a suspension which is stable for 90 days after opening associated to an administration of three or four doses of 3 mL to 20 mL per day may be stored into bottle of about 250 mL. The one skilled in the art will easily adapt the volume of the bottle to that needed as previously suggested.

The syringe is made of glass, plastic or any material convenient with the use and the storage of the liquid suspensions as disclosed herein. The syringe may be graduated to facilitate the administration of the liquid suspension. In an embodiment, the syringe is a 5 mL graduated syringe.

The cap (or closure) is any article for closing a suitably shaped opening. It encompasses, but is not limited to, childproof closures, waterproof closures, pipette-associated caps, solid caps, plastic or polymeric caps. In an embodiment, the cap is screwed on the bottle top or interlocked with the top of the bottle.

A sealing element may be required for the tightness of the system bottle-cap or bottle-pipette-cap or bottle-pipette, adapter or pipette-cap. This element can be supplied on its own and further fit in the bottle-neck, or around the pipette, or in the cap, or it can be previously adapted to the bottle, the cap or the pipette.

The invention also relates to a kit of parts comprising a package containing bottles of the liquid suspension formulation as disclosed herein and pipettes intended to remove the needed amount of the liquid formulation and/or instructions.

In another aspect, the invention relates to a kit of parts allowing the extemporaneously preparation of the suspensions according to the invention.

In an embodiment, the pharmaceutically acceptable container may be a bottle, wherein the bottle was selected from group consisting of a glass bottle and a plastic bottle. Examples of glass bottle include, but are not limited to Type 1, II and III borosilicate glass bottles. In an embodiment, the pharmaceutically acceptable container was a glass bottle, wherein the glass bottle may be amber color glass bottle or clear glass bottle. Examples of plastic bottles include, but are not limited to, high-density polyethylene (HDPE), polyethylene terephthalate (PET) and polypropylene (PP) bottles. In an embodiment, the pharmaceutically acceptable container is a plastic bottle, wherein the plastic bottle may be amber color, white opaque or translucent plastic bottle. In preferred embodiment, the HDPE bottles will be available in 30, 60, 120, 250 and 500-mL fill volumes.

In an embodiment, the pharmaceutical composition of present application was packed in a kit comprising bottle with child resistant cap, dosing syringe, adapter and dosing syringe.

Stability

As used herein, the term "stable" is defined as no more than about 5% loss of baclofen under typical commercial storage conditions. In certain embodiments, the formulations of the present invention will have no more than about 3% loss of baclofen, more preferably, no more than about 2% loss of baclofen, under typical commercial storage conditions. The composition retains at least about 95% of the potency of baclofen after storing the composition at 40° C. and 75% RH for at least three months. In certain aspects, the term "stable" refers to chemical stability, wherein not more than 5% w/w of total related substances are formed on storage at accelerated conditions of stability at 40° C. and 75% RH or at 25° C. and 60% RH or 2-8° C. for a period of at least six months or to the extent necessary for use of the composition.

In particular, the BRC-A impurity (i.e., 4-(4-Chlorophenyl)-2-pyrrolidinone) may be monitored. The structure of BRC-A impurity is shown below:

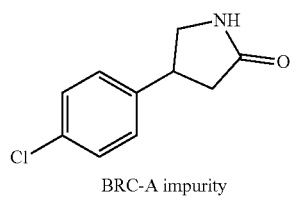 [SMILES: O=C1CC(c2ccc(Cl)cc2)CN1]

BRC-A impurity

Compositions of the present application were found to remain in suspension, without any agglomeration or sedimentation, when stored for at least 6 months at 2-8° C., or 25° C./60% RH condition or 40° C./75% RH conditions.

In another embodiment, the invention relates to liquid pharmaceutical composition of baclofen intended for oral administration comprising about 5 mg/mL baclofen, at least one suspending agent and at least one stabilizer, wherein the composition is stable for at least 6 months at any one of the following conditions, i.e., about 2-8° C. or at 25° C./60% RH condition or at 40° C./75% RH condition.

In another embodiment, the invention relates to stable aqueous suspensions of baclofen intended for oral administration comprising about 5 mg/mL baclofen, xanthan gum and hydroxypropyl methylcellulose, wherein the suspension is stable for at least 6 months at any one of the following conditions, i.e., about 2-8° C. or at 25° C./60% RH condition or at 40° C./75% RH condition.

In another embodiment, the invention relates to stable aqueous suspensions of baclofen intended for oral administration comprising about 5 mg/mL baclofen, at least one suspending agent and at least one stabilizer, wherein the suspension when stored for at least 6 months at any one of the following conditions, i.e., about 2-8° C. or at 25° C./60% relative humidity (RH) condition or at 40° C./75% relative humidity (RH) condition exhibits less than about 4% (w/w) of BRC-A impurity as measured by HPLC.

In an embodiment, the invention relates to stable aqueous suspensions of baclofen intended for oral administration comprising about 5 mg/mL baclofen and hydroxypropyl methylcellulose, wherein the suspension further comprises xanthan gum as suspending agent, and wherein pH of the aqueous suspension is in between 5-7.

Dosage and Administration

The pharmaceutical compositions as described herein may be used in methods of treatment, in which an effective amount of baclofen or a pharmaceutically acceptable salt thereof is administered to a patient.

For administration to animal or human subjects, the pharmaceutical compositions comprise an effective dosage amount of baclofen or a pharmaceutically acceptable salt thereof. The formulation may be prepared using conventional methods, for example, depending on the subject to be treated, the mode of administration, and the type of treatment desired (e.g., prevention, prophylaxis, or therapy).

In an embodiment of the present invention, the method for managing or treating or alleviating signs and symptoms of spasticity resulting from multiple sclerosis in a subject by administering a pharmaceutical composition comprising baclofen and one or more pharmaceutically acceptable excipients comprises stabilizers, suspending agents, sweetening agents, flavoring agents, preservatives, anti-oxidants, pH adjusting agents, buffering agents, coloring agents, anti-foaming agents, surfactants and combinations thereof.

In one embodiment, the present application relates to method of treating signs and symptoms of spasticity resulting from multiple sclerosis, spinal cord disease or spinal cord damage in a subject by administering a pharmaceutical composition comprising baclofen or its pharmaceutically acceptable salts thereof and a stabilizer, wherein particularly for the relief of flexor spasms and concomitant pain, clonus, and muscular rigidity.

Determination of baclofen optimal dosage may require individual titration. Therapy may be started at a low dosage, and increase gradually until an optimum effect is achieved (e.g., usually between 40-80 mg daily). In certain embodiments, 1-30 mL of baclofen oral suspension may be administered to achieve optimum effect, preferably 3-20 mL may be administered to achieve optimum effect.

In an embodiment, the present application relates to method of treating signs and symptoms of spasticity resulting from multiple sclerosis in adult patient, the method comprising administering 5 mg three times a day for 3 days or 10 mg three times a day for 3 days or 15 mg three times a day for 3 days or 20 mg three times a day for 3 days or additional increases may be necessary up to the maximum recommended dosage of 80 mg daily (20 mg four times a day) to the subject a pharmaceutical composition comprising baclofen or its pharmaceutically acceptable salts thereof.

In an embodiment, the present application relates to method of treating signs and symptoms of spasticity resulting from multiple sclerosis in patients of age less than 18 years with dose from 0.3 mg/kg a day to 2.5 mg/kg a day, in 2 to 4 divided doses to the subject a pharmaceutical composition comprising baclofen and one or more pharmaceutically acceptable excipients.

In certain aspects, the pharmaceutical compositions described herein may be used to treat adults and adolescents (e.g., about 13-17 years). In certain aspects, the pharmaceutical compositions described herein may be used as monotherapy or as adjunctive therapy. For example, additional active agents may be used in adjunctive therapy with baclofen, such as pain medications (e.g., morphine, hydromorphone, etc.).

The dosage levels can be dependent on the nature of the condition, drug efficacy, the condition of the patient, the judgment of the practitioner, and the frequency and mode of administration. The unit dosage forms can be administered to achieve any daily amount described herein, such as by administering one to five times daily (e.g., one, two, three, four, or five times daily).

EXAMPLES

The following examples are exemplary and not intended to be limiting. The above disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

General HPLC Procedure

As explained in detail below, the following HPLC procedure can be used to detect and quantify impurities of baclofen. The materials and general conditions are listed below:

Chromatographic Conditions

TABLE 1

| Column | Waters Symmetry C18, 250 X 4.6 mm, 5μ |
|---|---|
| Column Temperature | 35° C. |
| Flow rate | 1.0 mL/min |
| Detector | 225 nm with PDA/UV detector |
| Injection volume | 10 μL |
| Run time | 70 minutes |
| Mobile Phase A | Dissolve 1.38 g of potassium dihydrogen phosphate and 1.75 g of 1-pentane sulphonic acid sodium salt, anhydrous in 1000 mL of water, adjust the pH of solution to 3.0 ± 0.05 with o-phosphoric acid. |
| Mobile Phase B | mixture of acetonitrile and water in 20:80% v/v ratio. |

Gradient Program

TABLE 2

| Time (min) | % Mobile phase-A | % Mobile phase-B |
|---|---|---|
| 0.01 | 80 | 20 |
| 30 | 60 | 40 |
| 35 | 60 | 40 |
| 49 | 50 | 50 |
| 55 | 10 | 90 |
| 60 | 10 | 90 |
| 61 | 80 | 20 |
| 70 | 80 | 20 |

Example 1

Compositions of baclofen suspensions prepared are set forth in Table 3.

TABLE 3

| | Composition | |
|---|---|---|
| | A | B |
| Ingredients | Quantity/batch | |
| Baclofen | 5.00 gm | 2.50 gm |
| Avicel ® RC 591 | 12.00 gm | 7.50 gm |

TABLE 3-continued

| | Composition | |
|---|---|---|
| | A | B |
| Ingredients | Quantity/batch | |
| Methyl Paraben | 2.00 gm | 1.00 gm |
| Propyl Paraben | 0.20 gm | 0.10 gm |
| Sucralose | 3.00 gm | 1.50 gm |
| Mixed Berry Flavor | 2.00 gm | 1.00 gm |
| Purified Water | Up to 1000 mL | Up to 500 mL |

Manufacturing procedure of Composition A

About 550 mL of the purified water was heated to 60° C.±2° C. in a suitable container. Specified amounts of methyl paraben and propyl paraben were added to the purified water at 60° C.±2° C. and stirred continuously to obtain paraben solution.

The paraben solution was kept for cooling under continuous mixing until the temperature was reduced to 25° C.±2° C. Specified quantity of baclofen was added to the paraben solution and mixed continuously at a temperature of 25° C.±2° C. until a uniform dispersion was obtained. Specified quantities of sucralose and mixed berry flavor were added to the baclofen dispersion and mixed continuously at a temperature of 25° C.±2° C. for the next 15 minutes to obtain a sucralose solution In another suitable container, 400 mL of purified water was dispensed and the specified quantity of Avicel® RC 591 was added to water and mixed continuously at a temperature of 25° C.±2° C. to obtain an Avicel® RC 591 dispersion. The Avicel® RC 591 dispersion was homogenized on homogenizer. The Avicel RC 591 dispersion was added to the above sucralose solution and mixed continuously for the next 10 minutes to obtain a pre-final dispersion. The remaining amount of purified water was added to make up the pre-final dispersion to a volume of 1000 mL, and mixed to obtain a uniform final suspension.

Manufacturing Procedure of Composition B

About 350 mL of the purified water was heated to a temperature of 60° C.±2° C. in a suitable container. Specified amounts of methyl paraben and propyl paraben were added to the purified water at 60° C.±2° C. and stirred continuously to obtain a paraben solution. The paraben solution was kept for cooling under continuous mixing until the temperature was reduced to 25° C.±2° C. Specified quantity of baclofen was added to the paraben solution and mixed continuously at a temperature of 25° C.±2° C. until a uniform baclofen dispersion was obtained. Specified quantity of Avicel® RC 591 was added to the baclofen dispersion and mixed continuously at a temperature of 25° C.±2° C. for the next 5 minutes to obtain an Avicel® dispersion. The Avicel® dispersion was homogenized at temperature 25° C.±2° C. for 5 minutes.

In another suitable container, 100 mL of purified water was dispensed and specified quantities of sucralose and mixed berry flavor were added to the water and mixed continuously at a temperature of 25° C.±2° C. for 10 minutes to obtain a sucralose solution. The sucralose solution was added to the homogenized Avicel® dispersion and mixed continuously for the next 10 minutes to obtain a pre-final dispersion. The remaining amount of purified water was added to make up the pre-final dispersion to a volume of 500 mL and mixed to obtain a uniform final suspension.

Crystal growth was observed, when samples of Composition A and B were stored for 1 week at room temperature.

Example 2

Compositions of baclofen suspensions prepared are set forth in Table 4.

TABLE 4

| | Composition | |
|---|---|---|
| | C | D |
| Ingredients | Quantity/batch | |
| Baclofen | 2.50 gm | 5.00 gm |
| Xanthan Gum | 1.75 gm | 5.00 gm |
| Methyl Paraben | 1.00 gm | 2.00 gm |
| Propyl Paraben | 0.10 gm | 0.20 gm |
| Sucralose | 1.50 gm | 3.00 gm |
| Purified Water | Up to 500 mL | Up to 1000 mL |

Manufacturing Procedure of Composition C

About 300 mL of the purified water was heated to 60° C.±2° C. in a suitable container. Specified amounts of methyl paraben and propyl paraben were added to the purified water at 60° C.±2° C. and stirred continuously to obtain a paraben solution. The paraben solution was kept for cooling under continuous mixing until the temperature was reduced to 25° C.±2° C. Specified quantity of xanthan gum was added to the paraben solution and mixed continuously at temperature 25° C.±2° C. to obtain a xanthan gum solution.

In another suitable container, 120 mL of purified water was dispensed and specified quantity of sucralose was added to the water and mixed continuously at a temperature of 25° C.±2° C. for next 15 minutes to obtain a sucralose solution. Specified quantity of baclofen was added to sucralose solution and mixed continuously at a temperature of 25° C.±2° C. to obtain a uniform baclofen dispersion. The baclofen dispersion was added to the above xanthan gum solution and mixed continuously for the next 10 minutes to obtain a pre-final dispersion. The remaining amount of purified water was added to make up a pre-final dispersion to a volume of 500 mL and mixed to obtain a uniform final suspension.

Manufacturing Procedure of Composition D

About 700 mL of the purified water was heated to 60° C.±2° C. in a suitable container. Specified amount of methyl paraben and propyl paraben were added to the purified water at 60° C.±2° C. and stirred continuously to obtain a paraben solution. The paraben solution was kept for cooling under continuous mixing until the temperature was reduced to 25° C.±2° C. Specified quantity of xanthan gum was added to paraben solution and mixed continuously at temperature 25° C.±2° C. to obtain an xanthan gum solution. Specified quantity of baclofen was added to xanthan gum solution and mixed continuously at temperature 25° C.±2° C. to obtain a uniform baclofen dispersion In another suitable container, 100 mL of purified water was dispensed and specified quantity of sucralose was added to the water and mixed continuously at temperature 25° C.±2° C. for next 15 minutes to obtain a sucralose solution. The sucralose solution was added to the above baclofen dispersion and mixed continuously for next 10 minutes to obtain a pre-final dispersion. The remaining amount of purified water was added to make up a pre-final dispersion to a volume of 1000 mL and mixed to obtain a uniform final suspension.

Crystal growth was observed, when samples of Composition C and D were stored for 1 week at room temperature.

Example 3

Compositions of baclofen suspension were set forth in Table 5.

TABLE 5

| Ingredients | Composition E | Composition F |
|---|---|---|
| | Quantity/batch | |
| Baclofen | 5.00 gm | 5.00 gm |
| Avicel ® RC 591 | 12.00 gm | — |
| Xanthan gum | — | 5.00 gm |
| Xylitol | 200.00 gm | 150.00 gm |
| Methyl Paraben | 2.00 gm | 2.00 gm |
| Propyl Paraben | 0.20 gm | 0.20 gm |
| Sucralose | 3.00 gm | 3.00 gm |
| Purified Water | Up to 1000 mL | Up to 1000 mL |

Manufacturing Procedure of Composition E

About 400 mL of the purified water was heated to 60° C.±2° C. in a suitable container. Specified amounts of methyl paraben and propyl paraben were added to the purified water at 60° C.±2° C. and stirred continuously to obtain a paraben solution. The paraben solution was kept for cooling under continuous mixing until the temperature was reduced to 25° C.±2° C.

In another suitable container, 400 mL of purified water was dispensed and specified quantity of sucralose and xylitol were added to the water and mixing continuously to obtain a sucralose and xylitol solution. Specified quantity of Avicel® RC 591 was added to the sucralose and xylitol solution and mixed continuously at a temperature of 25° C.±2° C. to obtain a Avicel® RC 591 dispersion. Specified quantity of baclofen was added to the Avicel® dispersion and mixed continuously at a temperature of 25° C.±2° C. to obtain a uniform baclofen dispersion. The baclofen dispersion was homogenized on a homogenizer for better dispersion. The paraben solution was added to the homogenized baclofen dispersion and mixed continuously for the next 10 minutes to obtain a pre-final dispersion. The remaining amount of purified water was added to make up a pre-final dispersion to 1000 mL and mixed to obtain a uniform final suspension.

Manufacturing Procedure of Composition F

About 500 mL of the purified water was heated to 60° C.±2° C. in a suitable container. Specified amounts of methyl paraben and propyl paraben were added to the purified water at 60° C.±2° C. and stirred continuously to obtain a paraben solution. The paraben solution was kept for cooling under continuous mixing until the temperature was reduced to 25° C.±2° C. Specified quantity of xanthan gum was added to paraben solution and mixed continuously at temperature 25° C.±2° C. to obtain an xanthan gum solution.

In another suitable container, 400 mL of purified water was dispensed and specified quantities of sucralose and xylitol were added to the water and mixed continuously to obtain sucralose and xylitol solution. Specified quantity of baclofen was added to sucralose and xylitol solution and mixed continuously at a temperature of 25° C.±2° C. to obtain a uniform baclofen dispersion. The baclofen dispersion was homogenized on a homogenizer for better dispersion. The xanthan gum solution was added to the homogenized baclofen dispersion and mixed continuously for the next 10 minutes to obtain a pre-final dispersion. The remaining amount of purified water was added to make up a pre-final dispersion to a volume of 1000 mL, and mixed to obtain a uniform final suspension.

Crystal growth was observed, when samples of composition E and F were stored for 1 month at room temperature.

Example 4

The composition of the baclofen suspension prepared is set forth in Table 6.

TABLE 6

| Ingredients | Composition G Quantity/batch |
|---|---|
| Baclofen | 5.00 gm |
| Avicel ® RC 591 | 12.00 gm |
| Methyl Paraben | 2.00 gm |
| Propyl Paraben | 0.20 gm |
| Sucralose | 3.00 gm |
| Mixed Berry Flavor | 2.00 gm |
| HPMC | 5.00 gm |
| Purified Water | Up to 1000 mL |

Manufacturing Procedure of Composition G

About 700 mL of the purified water was heated to 60° C.±2° C. in a suitable container. Specified amounts of methyl paraben and propyl paraben were added to the purified water at 60° C.±2° C. and stirred continuously to obtain a paraben solution. The paraben solution was kept for cooling under continuous mixing until the temperature was reduced to 25° C.±2° C. Specified quantity of Avicel® RC 591 was added to paraben solution and mixed continuously at a temperature of 25° C.±2° C. to obtain a Avicel® dispersion In another suitable container, 200 mL of purified water was dispensed and specified quantity of sucralose and mixed berry flavor were added to the water and mixed continuously at a temperature of 25° C.±2° C. for 10 minutes to obtain a sucralose solution. Specified quantity of HPMC was added to sucralose solution and mixed continuously at a temperature of 25° C.±2° C. to obtain an HPMC solution. Specified quantity of baclofen was added to HPMC solution and mixed continuously at a temperature of 25° C.±2° C. to obtain a uniform baclofen dispersion. The baclofen dispersion was homogenized on a homogenizer for better dispersion. The homogenized baclofen dispersion was added to the Avicel® dispersion and mixed continuously for the next 10 minutes to obtain a pre-final dispersion. The remaining amount of purified water was added to make up a pre-final dispersion to a volume of 1000 mL and mixed to obtain a uniform final suspension.

After samples of composition G were stored for three months at room temperature, the baclofen was well dispersed, suspended and no crystal growth was observed in composition G.

Stability data of composition G was set forth in Table 7.

TABLE 7

| | Composition G | | | |
|---|---|---|---|---|
| Test Condition | RT | 40° C./ 75% RH | 40° C./ 75% RH | 25° C./ 60% RH |
| Period | Initial | 2 months | 3 months | 3 months |
| Description | No crystal growth observed | | | |
| PH | 6.29 | 6.12 | 6.05 | 6.27 |
| Assay | 98.8 | 97.7 | 97.7 | 97.8 |
| Related substances % w/w | | | | |
| BRC-A impurity | 0.121 | 0.17 | 0.17 | 0.14 |
| Maximum unknown Impurity | 0.005 | 0.007 | 0.006 | 0.005 |
| Total Impurity | 0.126 | 0.18 | 0.22 | 0.17 |

Dissolution data of composition G was set forth in Table 8.

TABLE 8

| Batch No. | Composition G |
|---|---|
| Dissolution Details | Dose: 4 mL equivalent to 20 mg of Baclofen, Volume 1000 mL, USP Apparatus-II, 50 RPM |
| Dissolution Media | 0.01N HCl (OGD) |

| Condition | RT | 40° C./75% RH |
|---|---|---|
| Period | Initial | 2 months |
| Time Point | % Drug release | |
| 10 minutes | 96.4 | 100.1 |
| 15 minutes | 97.4 | 99.0 |
| 20 minutes | 97.9 | 99.0 |
| 30 minutes | 98.1 | 99.6 |
| Infinity | 97.7 | 100.1 |

Example 5

Compositions of the baclofen suspensions that were prepared are set forth in Table 9.

TABLE 9

| | Composition | | | | | |
|---|---|---|---|---|---|---|
| Ingredients | H | I | J | K | L | M |
| | Quantity/batch | | | | | |
| Baclofen | 5.00 gm | 5.00 gm | 7.50 gm | 5.00 gm | 5.00 gm | 5.00 gm |
| Xanthan Gum | 5.00 gm | 3.50 gm | 5.25 gm | 3.50 gm | 3.00 gm | 3.00 gm |
| Methyl Paraben | 2.00 gm | 2.00 gm | 3.00 gm | 2.00 gm | 2.00 gm | 2.00 gm |
| Propyl Paraben | 0.20 gm | 0.20 gm | 0.30 gm | 0.20 gm | 0.20 gm | 0.20 gm |
| Sucralose | 3.00 gm | 3.00 gm | 4.50 gm | 3.00 gm | 3.00 gm | 3.00 gm |
| Grape Flavor | — | 2.00 gm | 3.00 gm | 2.00 gm | 2.00 gm | 2.00 gm |

TABLE 9-continued

| Ingredients | Composition | | | | | |
|---|---|---|---|---|---|---|
| | H | I | J | K | L | M |
| HPMC | 5.00 gm | 10.00 gm | 15.00 gm | 15.00 gm | 5.00 gm | 10.00 gm |
| Simethicone emulsion (30%) | — | 2.00 gm | 3.00 gm | 2.00 gm | 2.00 gm | 2.00 gm |
| Purified Water | Up to 1000 mL | Up to 1000 mL | Up to 1500 mL | Up to 1000 mL | Up to 1000 mL | Up to 1000 mL |

Manufacturing Procedure of Composition H

About 650 mL of the purified water was heated to 60° C.±2° C. in a suitable container. Specified amounts of methyl paraben and propyl paraben were added to the purified water at 60° C.±2° C. and stirred continuously to obtain a paraben solution. The paraben solution was kept for cooling under continuous mixing until the temperature was reduced to 25° C.±2° C. Specified quantity of xanthan gum was added to the paraben solution and mixed continuously at temperature 25° C.±2° C. to obtain a xanthan gum solution.

In another suitable container, 200 mL of purified water was dispensed and specified quantity of sucralose was added and mixed continuously at temperature 25° C.±2° C. for next 10 minutes to obtain a sucralose solution. Specified quantity of HPMC was added to the sucralose solution and mixed continuously at temperature 25° C.±2° C. to obtain a HPMC solution. Specified quantity of baclofen was added to the HPMC solution with continuous homogenization at temperature 25° C.±2° C. to obtain a uniform baclofen dispersion. The baclofen dispersion was added to the above xanthan gum solution and mixed continuously for next 10 minutes to obtain a pre-final dispersion. The remaining amount of purified water was added to make up the pre-final dispersion to a volume of 1000 mL and mixed to obtain a uniform final suspension.

Manufacturing Procedure of Composition I, J, K, L and M

About 650 mL of the purified water was heated to 60° C.±2° C. in a suitable container. Specified amounts of methyl paraben and propyl paraben were added to the purified water at 60° C.±2° C. and stirred continuously to obtain a paraben solution. The paraben solution was kept for cooling under continuous mixing until the temperature was reduced to 25° C.±2° C. Specified quantity of xanthan gum was added to the paraben solution and mixed continuously at temperature 25° C.±2° C. to obtain an xanthan gum solution.

In another suitable container, 250 mL of purified water was dispensed and specified quantities of sucralose and grape flavor were added and mixed continuously at a temperature of 25° C.±2° C. for the next 10 minutes to obtain a sucralose solution. Specified quantity of simethicone was added to the sucralose solution and mixed continuously for 10 minutes at a temperature of 25° C.±2° C. to obtain a simethicone solution. Specified quantity of HPMC was added to the simethicone solution and mixed continuously at a temperature 25° C.±2° C. to obtain an HPMC solution. Specified quantity of baclofen was added to HPMC solution with continuous homogenization at a temperature of 25° C.±2° C. to obtain a uniform baclofen dispersion. The baclofen dispersion was added to the above xanthan gum solution and mixed continuously for the next 10 minutes to obtain a pre-final dispersion. The remaining amount of purified water was added to make up the pre-final dispersion to a volume of 1000 mL and mixed to obtain a uniform final suspension.

After samples of Composition H, I, J, K, L and M were stored for two months at room temperature, the baclofen is well dispersed, suspended and no crystal growth was observed in all Composition H, I, J, K, L and M.

Stability data of Composition H and I were set forth in Table 10:

TABLE 10

| Test | Composition H | | | | Composition | | | |
|---|---|---|---|---|---|---|---|---|
| Condition | RT | 40° C./ 75% RH | 40° C./ 75% RH | 25° C./ 60% RH | RT | 40° C./ 75% RH | 40° C./ 75% RH | 25° C./ 60% RH |
| Period | Initial | 2M | 3M | 3M | Initial | 2M | 3M | 3M |
| Description | Translucent Suspension, no crystal growth observed | | | | | | | |
| pH | 6.26 | 5.94 | 5.79 | 6.19 | 5.76 | 5.71 | 5.62 | 5.66 |
| PSD-D90 (µ) | 33 | 31.3 | 35 | 29.8 | 34 | 35 | 33 | 33.9 |
| Assay | 97.5 | 101.8 | 102.2 | 100.9 | 103.4 | 101.5 | 104 | 102.4 |
| Related substances % w/w | | | | | | | | |
| Impurity A | 0.017 | 0.05 | 0.081 | 0.021 | 0.018 | 0.054 | 0.118 | 0.03 |
| Maximum unknown Impurity | 0.003 | 0.004 | ND | ND | ND | 0.004 | 0.013 | 0.009 |
| Total Impurity | 0.028 | 0.064 | 0.081 | 0.021 | 0.018 | 0.07 | 0.131 | 0.039 |

Stability data of Composition J & K were set forth in Table 11:

TABLE 11

| Test | Composition J | | | | Composition K | | | |
|---|---|---|---|---|---|---|---|---|
| Condition | RT | 40° C./75% RH | 40° C./75% RH | 25° C./60% RH | RT | 40° C./75% RH | 40° C./75% RH | 25° C./60% RH |
| Period | Initial | 2M | 3M | 3M | Initial | 2M | 3M | 3M |
| Description | | | | No crystal growth observed | | | | |
| pH | 5.73 | 5.60 | 5.55 | 5.7 | 5.78 | 5.64 | 5.54 | 5.7 |
| PSD-D90 (μ) | 34.5 | 33.4 | 32.7 | 30.5 | 33.7 | 31.6 | 29.9 | 32.7 |
| Assay | 101.7 | 103.6 | 103.6 | 104.9 | 105.7 | 101.1 | 101.1 | 103.3 |
| | | | | Related substances % w/w | | | | |
| Impurity A | 0.018 | 0.052 | 0.115 | 0.032 | 0.028 | 0.06 | 0.113 | 0.034 |
| Maximum unknown Impurity | 0.005 | 0.003 | 0.007 | 0.008 | 0.008 | 0.007 | 0.007 | 0.007 |
| Total Impurity | 0.022 | 0.066 | 0.122 | 0.04 | 0.036 | 0.075 | 0.12 | 0.041 |

Stability data of Composition L & M were set forth in Table 12:

TABLE 12

| Test | Composition L | | | Composition M | | |
|---|---|---|---|---|---|---|
| Condition | RT | 40° C./75% RH | 25° C./60% RH | RT | 40° C./75% RH | 25° C./60% RH |
| Period | Initial | 3M | 3M | Initial | 3M | 3M |
| Description | | No crystal growth observed | | | No crystal growth observed | |
| pH | 5.74 | 5.52 | 5.63 | 5.75 | 5.51 | 5.65 |
| PSD-D90 (μ) | 35.3 | 32.4 | 46.2 | 34.5 | 43.3 | 33.8 |
| Assay | 104.3 | 103.1 | 103.8 | 103.9 | 103.3 | 103.7 |
| | | | Related substances % w/w | | | |
| Impurity A | 0.024 | 0.113 | 0.034 | 0.022 | 0.118 | 0.032 |
| Maximum unknown Impurity | 0.009 | 0.006 | 0.01 | 0.008 | 0.008 | 0.01 |
| Total Impurity | 0.033 | 0.119 | 0.044 | 0.03 | 0.126 | 0.042 |

Dissolution data of composition I was set forth in Table 13.

TABLE 13

| Batch No. | Composition I |
|---|---|
| Dissolution Details | Dose: 4 mL equivalent to 20 mg of Baclofen, Volume 1000 mL, App-2, 50 RPM |
| Dissolution Details Media | 0.01N HCl (OGD) |
| Condition | RT |
| Period | Initial |
| Time Point | % Drug release |
| 10 minutes | 100.6 |
| 15 minutes | 101.1 |
| 20 minutes | 101.1 |
| 30 minutes | 100.9 |
| Infinity | 101.0 |

Dissolution data of composition J was set forth in Table 14.

TABLE 14

| Batch No. | Composition J | | |
|---|---|---|---|
| Dissolution Details | Dose: 4 ml equivalent to 20 mg of Baclofen, Volume 1000 ml, App-2, 50 RPM | | |
| Dissolution Media | 0.01N HCl | pH 4.5 acetate buffer | pH 6.8 phosphate buffer |
| Condition | RT | RT | RT |
| Period | Initial | Initial | Initial |
| Time Point | % Drug release | | |
| 5 min | 98.1 | 97.8 | 102.3 |
| 10 min | 99.6 | 100.2 | 102.5 |
| 15 min | 100.1 | 100.4 | 103.6 |
| 20 min | 100.5 | 100.1 | 102.7 |
| 30 min | 100.5 | 100.0 | 102.7 |
| Infinity | 101.1 | 100.1 | 102.1 |

Example 6

A composition of baclofen suspension prepared is set forth in Table 15.

TABLE 15

| Ingredients | Composition N Quantity in grams/batch |
|---|---|
| Baclofen | 2.500 |
| Xanthan Gum | 1.750 |
| Methyl Paraben | 1.000 |
| Propyl Paraben | 0.100 |
| Sucralose | 1.500 |
| Grape Flavor | 1.000 |
| HPC | 5.000 |
| Simethicone emulsion (30%) | 1.000 |
| Purified Water | Up to 500 mL |

Manufacturing Procedure of Composition N:

About 300 mL of the purified water was heated to 60° C.±2° C. in a suitable container. Specified amounts of methyl paraben and propyl paraben were added to the purified water at 60° C.±2° C. and stirred continuously to obtain a paraben solution. The paraben solution was kept for cooling under continuous mixing until the temperature was reduced to 25° C.±2° C. Specified quantity of xanthan gum was added to the paraben solution and mixed continuously at a temperature of 25° C.±2° C. to obtain an xanthan gum solution.

In another suitable container, 150 mL of purified water was dispensed and specified quantities of sucralose and grape flavor were added and mixed continuously at temperature 25° C.±2° C. for the next 10 minutes to obtain a sucralose solution. Specified quantity of simethicone was added to the sucralose solution and mixed continuously for 10 minutes at a temperature of 25° C.±2° C. to obtain a simethicone solution. Specified quantity of HPC was added to the simethicone solution and mixed continuously at a temperature of 25° C.±2° C. to obtain an HPC solution. Specified quantity of baclofen was added to the HPC solution with continuous homogenization at a temperature of 25° C.±2° C. to obtain a uniform baclofen dispersion. The baclofen dispersion was added to the above xanthan gum solution and mixed continuously for the next 10 minutes to obtain a pre-final dispersion. The remaining amount of purified water was added to make up the pre-final dispersion to a volume of 500 mL and mixed to obtain a uniform final suspension.

After samples of Composition N were stored for one month at room temperature, the baclofen is well dispersed, suspended and no crystal growth was observed in all composition N.

Stability data of Composition N are set forth in Table 16.

TABLE 16

| Test | Composition N | | |
|---|---|---|---|
| Condition | RT | 60° C. | 40° C./75% RH |
| Period | Initial | 2 weeks | 1 month |
| Description | No crystal growth observed | | |
| pH | 5.88 | ND | 5.73 |
| PSD-D90 (μ) | 32.9 | ND | 25.8 |
| Assay | 100.9 | ND | 101.8 |
| Related substances % w/w | | | |
| BRC-A impurity | 0.021 | 0.228 | 0.043 |
| Maximum unknown Impurity | ND | 0.009 | ND |
| Total Impurity | 0.021 | 0.25 | 0.043 |

Example 7

Compositions of baclofen suspension prepared are set forth in Table 17.

TABLE 17

| Ingredients | Composition O Quantity/batch | Composition P Quantity/batch |
|---|---|---|
| Baclofen | 2.500 | 2.500 |
| Xanthan Gum | 1.750 | 1.750 |
| Methyl Paraben | 1.000 | — |
| Propyl Paraben | 0.100 | — |
| Sucralose | 1.500 | 1.500 |
| Grape Flavor | 1.000 | 1.000 |
| Poloxamer 188 | 2.000 | — |
| PVP K-30 | — | 2.00 |
| Simethicone emulsion (30%) | 1.000 | 1.000 |
| Purified Water | Up to 500 mL | Up to 500 mL |

Manufacturing Procedure of Composition O:

About 300 mL of the purified water was heated to 60° C.±2° C. in a suitable container. Specified amounts of methyl paraben and propyl paraben were added to the purified water at 60° C.±2° C. and stirred continuously to obtain a paraben solution. The paraben solution was kept for cooling under continuous mixing until the temperature was reduced to 25° C.±2° C. Specified quantity of xanthan gum was added to the paraben solution and mixed continuously at a temperature of 25° C.±2° C. to obtain an xanthan gum solution.

In another suitable container, 150 mL of purified water was dispensed and specified quantities of sucralose and grape flavor were added and mixed continuously at a temperature of 25° C.±2° C. for the next 10 minutes to obtain a sucralose solution. Specified quantity of simethicone was added to the sucralose solution and mixed continuously for 10 minutes at a temperature of 25° C.±2° C. to obtain a simethicone solution. Specified quantity of poloxamer 188 was added to the simethicone solution and mixed continuously at a temperature of 25° C.±2° C. to obtain a poloxamer solution. Specified quantity of baclofen was added to the poloxamer solution with continuous homogenization at a temperature of 25° C.±2° C. to obtain a uniform baclofen dispersion. The baclofen dispersion was added to the above xanthan gum solution and mixed continuously for next 10 minutes to obtain a pre-final dispersion. The remaining amount of purified water was added to make up the pre-final dispersion to a volume of 500 mL and mixed to obtain a uniform final suspension.

Manufacturing Procedure of Composition P:

About 300 mL of the purified water was heated to 60° C.±2° C. in a suitable container. Specified quantity of xanthan gum was added to paraben solution and mixed continuously at a temperature of 25° C.±2° C. to obtain an xanthan gum solution.

In another suitable container, 150 mL of purified water was dispensed and specified quantities of sucralose and grape flavor were added and mixed continuously at a temperature of 25° C.±2° C. for the next 10 minutes to obtain a sucralose solution. Specified quantity of simethicone was added to the sucralose solution and mixed continuously for 10 minutes at a temperature of 25° C.±2° C. to obtain a simethicone solution. Specified quantity of PVP K30 was added to the simethicone solution and mixed continuously at a temperature of 25° C.±2° C. to obtain a PVP solution. Specified quantity of baclofen was added to the PVP solution with continuous homogenization at a temperature of 25°

C.±2° C. to obtain a uniform baclofen dispersion. The baclofen dispersion was added to the above xanthan gum solution and mixed continuously for the next 10 minutes to obtain a pre-final dispersion. The remaining amount of purified water was added to make up the pre-final dispersion to a volume of 500 mL and mixed to obtain a uniform final suspension.

After samples of Composition O and P were stored for one month at room temperature, the baclofen is well dispersed, suspended and no crystal growth was observed in Composition O and P.

Stability data of Composition O and P were set forth in Table 18.

added to the sucralose solution and mixed continuously for 10 minutes at a temperature of 25° C.±2° C. to obtain a simethicone solution. Specified quantity of HPMC was added to the simethicone solution and mixed continuously at a temperature of 25° C.±2° C. to obtain an HPMC solution. Specified quantity of baclofen was added to the HPMC solution with continuous homogenization at a temperature of 25° C.±2° C. to obtain an uniform baclofen dispersion. The baclofen dispersion was added to the above xanthan gum solution and mixed continuously for next 10 minutes to obtain a pre-final dispersion. The remaining amount of

TABLE 18

| Test | Composition O | | | Composition P | | |
|---|---|---|---|---|---|---|
| Condition | RT | 60° C. | 40° C./75% RH | RT | 60° C. | 40° C./75% RH |
| Period | Initial | 2 weeks | 1 month | Initial | 2 weeks | 1 month |
| Description | No crystal growth observed | | | | | |
| pH | 5.86 | ND | 5.66 | 5.78 | ND | 5.19 |
| PSD-D90 (μ) | 32.9 | ND | 31.7 | 30.5 | ND | 26.6 |
| Assay | 103.2 | ND | 103.6 | 101.3 | ND | 100.0 |
| Related substances % w/w | | | | | | |
| BRC-A impurity | 0.015 | 0.18 | 0.039 | 0.09 | 0.17 | 0.071 |
| Maximum unknown Impurity | ND | 0.007 | ND | 0.595 | 0.02 | 1.50 |
| Total Impurity | 0.015 | 0.2 | 0.039 | 0.945 | 0.21 | 2.32 |

Example 8

Compositions of baclofen suspensions prepared are set forth in Table 19.

TABLE 19

| Ingredients | Composition Q | Composition R |
|---|---|---|
| | Quantity/batch (batch size = 500 mL) | |
| Baclofen | 2.50 gm | 2.50 gm |
| Xanthan Gum | 1.75 gm | 1.75 gm |
| Methyl Paraben | 1.00 gm | 1.00 gm |
| Propyl Paraben | 0.10 gm | 0.10 gm |
| Sucralose | 1.50 gm | 1.50 gm |
| Grape Flavor | 1.00 gm | 1.00 gm |
| HPMC | 5.00 gm | 5.00 gm |
| Simethicone emulsion (30%) | 1.00 gm | 1.00 gm |
| pH 4 Citrate buffer | Up to 500 mL | — |
| pH 6.4 Phosphate buffer | — | Up to 500 mL |

Manufacturing Procedure of Composition Q:

About 300 mL of the pH 4 citrate buffer was heated to 60° C.±2° C. in a suitable container. Specified amounts of methyl paraben and propyl paraben were added to the purified water at 60° C.±2° C. and stirred continuously to obtain a paraben solution. The paraben solution was kept for cooling under continuous mixing until the temperature was reduced to 25° C.±2° C. Specified quantity of xanthan gum was added to paraben solution and mixed continuously at a temperature of 25° C.±2° C. to obtain an xanthan gum solution.

In another suitable container, 150 mL of pH 4 citrate buffer was dispensed and specified quantities of sucralose and grape flavor were added and mixed continuously at temperature 25° C.±2° C. for next 10 minutes to obtain a sucralose solution. Specified quantity of simethicone was purified water was added to make up the pre-final dispersion to a volume of 500 mL and mixed to obtain uniform final suspension.

Manufacturing Procedure of Composition R:

About 300 mL of the pH 6.4 phosphate buffer was heated to 60° C.±2° C. in a suitable container. Specified amounts of methyl paraben and propyl paraben were added to the purified water at 60° C.±2° C. and stirred continuously to obtain a paraben solution. The paraben solution was kept for cooling under continuous mixing until the temperature was reduced to 25° C.±2° C. Specified quantity of xanthan gum was added to the paraben solution and mixed continuously at a temperature of 25° C.±2° C. to obtain an xanthan gum solution.

In another suitable container, 150 mL of pH 6.4 phosphate buffer was dispensed and specified quantities of sucralose and grape flavor were added and mixed continuously at a temperature of 25° C.±2° C. for the next 10 minutes to obtain a sucralose solution. Specified quantity of simethicone was added to the sucralose solution and mixed continuously for 10 minutes at a temperature of 25° C.±2° C. to obtain a simethicone solution. Specified quantity of HPMC was added to the simethicone solution and mixed continuously at a temperature of 25° C.±2° C. to obtain an HPMC solution. Specified quantity of baclofen was added to the HPMC solution with continuous homogenization at a temperature of 25° C.±2° C. to obtain a uniform baclofen dispersion. The baclofen dispersion was added to the above xanthan gum solution and mixed continuously for the next 10 minutes to obtain a pre-final dispersion. The remaining amount of purified water was added to make up the pre-final dispersion to a volume of 500 mL and mixed to obtain a uniform final suspension.

After samples of Composition Q and R were stored for one month at room temperature, the baclofen is well dispersed, suspended and no crystal growth was observed in all Composition Q and R.

Stability data for Compositions Q and R is set forth in Table 20.

TABLE 20

| Test | Composition Q | | Composition R | |
|---|---|---|---|---|
| Condition | RT | 40° C./75% RH | RT | 40° C./75% RH |
| Period | Initial | 1M | Initial | 1M |
| Description | No crystal growth observed | | | |
| pH | 4.01 | 4.14 | 6.25 | 6.35 |
| PSD-D90 (µ) | ND | ND | ND | ND |
| Assay | 101.1 | 97.4 | 101.8 | 98.5 |
| Related substances % w/w | | | | |
| BRC-A impurity | 0.047 | 0.46 | 0.018 | 0.051 |
| Maximum unknown impurity | 0.142 | 0.64 | ND | 0.009 |
| Total impurity | 0.24 | 2.58 | 0.18 | 0.069 |

Example 9

Compositions of baclofen suspension prepared are set forth in Table 21.

TABLE 21

| | Composition S | | |
|---|---|---|---|
| Ingredients | Quantity per mL (mg) | % w/w | Quantity (kg) for 400 kg batch |
| Baclofen | 5.0 | 0.50 | 2.00 |
| Sucralose | 3.0 | 0.30 | 1.20 |
| Grape Flavor | 2.0 | 0.20 | 0.80 |
| Methyl Paraben | 2.0 | 0.20 | 0.80 |
| Propyl Paraben | 0.2 | 0.02 | 0.08 |
| Xanthan Gum | 3.5 | 0.35 | 1.40 |
| Hydroxy propyl methyl cellulose - 5 cps | 10.00 | 1.00 | 4.00 |
| Simethicone emulsion (30%) | 0.5 | 0.05 | 0.20 |
| Sodium Hydroxide | q.s. to adjust pH | — | q.s. to adjust pH |
| Hydrochloric acid | q.s. to adjust pH | — | q.s. to adjust pH |
| Purified water | q.s. to 1 mL | Up to 100 | q.s. to 400 kg |

Manufacturing Procedure of Composition S (Represented as FIGS. 1 & 2):

I. Dispensing:

The raw material was dispensed as per manufacturing formula for batch at not more than a temperature of 25° C. and a relative humidity of NMT 65% RH.

II. Compounding:

The entire compounding process was performed at a controlled room temperature of 25° C.±5° C.

a) Phase I Preparation (Methyl Paraben, Propyl Paraben, Xanthan Gum and HPMC Phase)
  i) Collected 67.25% of batch size of purified water (269 kg) in the 600 L jacketed manufacturing vessel. Heated collected purified water to 65° C.±5° C. with continuous stirring.
  ii) Addition of Methyl Paraben and Propyl paraben: Added and dispensed specified quantity of methylparaben in jacketed manufacturing vessel with continuous stirring, at 65° C.±5° C. Rinsed the bag with 0.5 kg of purified water and added to main jacketed manufacturing vessel. Added dispensed quantity of propylparaben in jacketed manufacturing vessel with continuous stirring, at 65° C.±5° C. Rinsed the bag with 0.5 kg of purified water and added to main jacketed manufacturing vessel. Cooled the solution to 25° C.±5° C. with continuous stirring.
  iii) Addition of Xanthan Gum: Added dispensed quantity of xanthan gum in jacketed manufacturing vessel with continuous stirring, at 25° C.±5° C. Stirred dispersion until no lumps were observed.
  iv) Addition of Hydroxypropyl Methylcellulose: Added dispensed quantity of hydroxypropyl methylcellulose in jacketed manufacturing vessel with continuous stirring, at 25° C.±5° C.

b) Phase II Preparation (API Phase)
  i) Collected around 20% of batch size of purified water (80.0 kg) in the 300 L capacity vessel.
  ii) Addition of Simethicone Emulsion (30%): Added dispensed quantity of simethicone emulsion in 300 L capacity vessel with continuous stirring, at 25° C.±5° C. Rinsed the container with 0.5 kg of purified water and added to 300 L capacity vessel.
  iii) Addition of Baclofen: Added dispensed quantity of baclofen in 300 L capacity vessel with continuous stirring, at 25° C.±5° C. Rinsed the bag with 0.5 kg of purified water and added to 300 L capacity vessel. Homogenize dispersion in the 300 L capacity vessel using a homogenizer to form a uniform dispersion.

c) Addition of Phase II Dispersion (API Phase) to Main Vessel
  i) Added API Phase to Phase I (methyl paraben, propyl paraben, xanthan gum and HPMC Phase) in jacketed manufacturing vessel with continuous stirring at 25° C.±5° C. Rinsed the 300 L capacity vessel twice with 10 kg of purified water and added to main jacketed manufacturing vessel to obtain a pre-final baclofen suspension.

d) Phase III Preparation (Sucralose and Grape Flavor)
  i) Collected around 2% of batch size of purified water (6.0 kg) in the 300 L stainless steel (SS) vessel.
  ii) Addition of Sucralose: Added dispensed quantity of sucralose in SS vessel. Mixed manually with the help of SS spatula, at 25° C.±5° C. and continued stirring until a clear solution was observed.
  iii) Addition of Grape Flavor: Added dispensed quantity of grape flavor in SS vessel, at 25° C.±5° C. Rinsed the container with 1.0 kg of purified water and added to SS vessel. Stirred the dispersion manually till a clear solution was observed.

e) Addition of Phase III Preparation (Sucralose and Grape Flavor) to Main Jacketed Vessel
  i) Added Phase Ill preparation (sucralose and grape flavor) from SS vessel to pre-final baclofen suspension of the main jacketed manufacturing vessel with continuous stirring at 25° C.±5° C. Rinsed the SS vessel with 1.0 kg of purified water and added to main jacketed manufacturing vessel. Stirred dispersion for 10 minutes.
  ii) Addition of Purified water: Added required quantity of purified water to jacketed manufacturing vessel with continuous stirring at 25° C.±5° C. to make up the volume up to 98% of batch size. Continued stirring of suspension for next 15 minutes.
  iii) PH Adjustment: Checked pH of suspension. If the pH is observed between 5.80 to 6.20, pH adjustment is not necessary. In case pH is outside this range, adjusted the pH of suspension to 5.80 to 6.20 (target 6.00) by using 1N sodium hydroxide or 1N hydrochloric acid. Mixed the suspension for not less than 15 minutes under continuous stirring.

iv) Volume Make up: Added required quantity of purified water to jacketed manufacturing vessel with continuous stirring at 25° C.±5° C. to make up the volume up to 100% of batch size. Continued stirring of suspension for next 15 minutes.

v) Filtration: Filtered the suspension through mesh #40 SS sieve and collected in SS storage tank.

vi) Packaging: Labelled and packed batch in 250 CC translucent HDPE bottles and sealed with 28 mm child-resistant (CR) cap. Each bottle to be filled with 250 mL baclofen oral suspension 5 mg/ml, followed by capping.

Thus, the present invention provides high-concentration, aqueous suspensions of baclofen, which are stable under a variety of storage conditions and for extended periods of time.

Having now fully described this invention, it will be understood by those of ordinary skill in the art that it can be performed within a wide equivalent range of parameters without affecting the scope of the invention or any embodiment thereof. All publications, patent applications and patents disclosed herein are incorporated by reference in their entirety.

Unless specified otherwise, all the percentages, portions and ratios in the present invention are on weight basis.

Unless otherwise indicated, all numbers expressing quantities of ingredients, properties such as molecular weight, reaction conditions, and so forth used in the present specification and associated claims are to be understood as being modified in all instances by the term "about." The terms "about" and "approximate," when used along with a numerical variable, generally means the value of the variable and all the values of the variable within a measurement or an experimental error (e.g., 95% confidence interval for the mean) or within a specified value (e.g., ±10%) within a broader range.

Accordingly, unless indicated to the contrary, the numerical parameters set forth in the following specification and attached claims are approximations that may vary depending upon the desired properties sought to be obtained by the embodiments of the present invention. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces.

While compositions and methods are described herein in terms of "comprising" various components or steps, the compositions and methods can also "consist essentially of" or "consist of" the various components and steps.

What is claimed is:

1. A stable liquid suspension comprising:
   a. a therapeutically effective amount of baclofen;
   b. at least one stabilizer; and
   c. at least one pharmaceutically acceptable liquid vehicle;
   wherein a concentration of the baclofen is 2 mg/mL or more;
   wherein the suspension is in the form of a ready-to-use liquid suspension or a ready-to-administer liquid suspension that is suitable for oral administration to a subject in need thereof; and
   wherein no crystal growth is observed when the suspension was stored for 3 months at 40° C./75% RH.

2. The suspension according to claim 1, further comprising one or more pharmaceutically acceptable excipients selected from the group consisting of pH adjusting agents, buffering agents, solubilizers, suspending agents, antioxidants, antifoaming agents, chelating agents, preservatives, flavoring agents, sweetening agents, coloring agents, surfactants, and mixtures thereof.

3. The suspension according to claim 2, wherein the one or more pharmaceutically acceptable excipients comprise an anti-foaming agent, and further wherein the antifoaming agent is a simethicone emulsion.

4. The suspension according to claim 1, wherein the suspension is an aqueous suspension.

5. The suspension according to claim 1, wherein the suspension has a pH between about 4 to about 8.

6. The suspension according to claim 1, wherein the suspension has a pH between about 5 to about 7.

7. A method for managing, treating, or alleviating the signs and symptoms of spasticity resulting from multiple sclerosis, spinal cord damage or spinal cord disease in a patient in need thereof by orally administering a therapeutically effective amount of the suspension according to claim 1.

8. The suspension according to claim 1, wherein the at least one stabilizer is selected from the group consisting of hydroxypropyl methylcellulose (HPMC), hydroxypropyl cellulose (HPC), povidone (PVP K-30), poloxamer and mixtures thereof.

9. The suspension according to claim 1, wherein a level of total impurities is less than about 2% (w/w) as measured by HPLC when stored for one month at 40° C./75% RH.

10. The suspension according to claim 1, wherein a level of (4-(4-chlorophenyl)-2-pyrrolidinone is less than about 0.5% (w/w) as measured by HPLC when stored for 3 months at 40° C./75% RH.

11. A stable liquid suspension comprising:
   a. a therapeutically effective amount of baclofen;
   b. at least one stabilizer; and
   c. at least one pharmaceutically acceptable liquid vehicle;
   wherein a concentration of the baclofen is 2 mg/mL or more;
   wherein the suspension is in the form of a ready-to-use liquid suspension or a ready-to-administer liquid suspension that is suitable for oral administration to a subject in need thereof, and
   wherein a level of (4-(4-chlorophenyl)-2-pyrrolidinone is less than about 2% (w/w) as measured by HPLC when stored for 3 months at 40° C./75% RH.

12. The suspension according to claim 11, further comprising one or more pharmaceutically acceptable excipients selected from the group consisting of pH adjusting agents, buffering agents, solubilizers, suspending agents, antioxidants, antifoaming agents, chelating agents, preservatives, flavoring agents, sweetening agents, coloring agents, surfactants, and mixtures thereof.

13. The suspension according to claim 11, wherein the suspension has a pH between about 4 to about 8.

14. The suspension according to claim 11, wherein the suspension has a pH between about 5 to about 7.

15. A method for managing, treating, or alleviating the signs and symptoms of spasticity resulting from multiple sclerosis, spinal cord damage or spinal cord disease in a patient in need thereof by orally administering a therapeutically effective amount of the suspension according to claim 11.

16. The suspension according to claim 11, wherein a level of (4-(4-chlorophenyl)-2-pyrrolidinone is less than about 1% (w/w) as measured by HPLC when stored for 3 months at 40° C./75% RH.

17. The suspension according to claim 11, wherein a level of (4-(4-chlorophenyl)-2-pyrrolidinone is less than about 0.5% (w/w) as measured by HPLC when stored for 3 months at 40° C./75% RH.

18. The suspension according to claim 11, wherein the stabilizer is selected from the group consisting of hydroxypropyl methylcellulose (HPMC), hydroxypropyl cellulose (HPC), povidone (PVP K-30), poloxamer and mixtures thereof.

19. The suspension according to claim 11, wherein the baclofen is present at a concentration of about 5 mg/mL.

\* \* \* \* \*